(12) United States Patent
Koo

(10) Patent No.: US 10,245,172 B2
(45) Date of Patent: Apr. 2, 2019

(54) WEARABLE NOXIPOINTS STIMULATING DEVICES

(71) Applicant: Charles C. Koo, Palo Alto, CA (US)

(72) Inventor: Charles C. Koo, Palo Alto, CA (US)

(*) Notice: Subject to any disclaimer, the term of this patent is extended or adjusted under 35 U.S.C. 154(b) by 0 days.

(21) Appl. No.: 15/804,932

(22) Filed: Nov. 6, 2017

(65) Prior Publication Data
US 2018/0055674 A1    Mar. 1, 2018

Related U.S. Application Data

(63) Continuation-in-part of application No. 15/620,529, filed on Jun. 12, 2017, now Pat. No. 9,814,616, which is a continuation of application No. 14/631,781, filed on Feb. 25, 2015, now Pat. No. 9,713,543, which is a continuation-in-part of application No. 13/396,605, filed on Feb. 15, 2012, now Pat. No. 9,205,256.

(60) Provisional application No. 61/443,258, filed on Feb. 16, 2011, provisional application No. 61/944,216, filed on Feb. 25, 2014.

(51) Int. Cl.
*A61N 1/00* (2006.01)
*A61F 5/02* (2006.01)
*A61K 38/18* (2006.01)
*A61N 1/36* (2006.01)
*A61K 38/19* (2006.01)
*A61F 5/01* (2006.01)
*A61K 31/165* (2006.01)
*A61N 1/04* (2006.01)

(52) U.S. Cl.
CPC .............. *A61F 5/02* (2013.01); *A61F 5/013* (2013.01); *A61K 31/165* (2013.01); *A61K 38/18* (2013.01); *A61K 38/1833* (2013.01); *A61K 38/191* (2013.01); *A61N 1/3603* (2017.08); *A61N 1/36021* (2013.01); *A61N 1/0476* (2013.01); *A61N 1/36034* (2017.08); *A61N 1/36042* (2013.01)

(58) Field of Classification Search
CPC ..................................................... A61N 1/0404
USPC ............................................. 607/46, 48, 50
See application file for complete search history.

*Primary Examiner* — Nadia A Mahmood
(74) *Attorney, Agent, or Firm* — Haverstock & Owens LLP

(57) ABSTRACT

Wearable devices for Noxipoints stimulation have a wearable member containing a grid of electrodes. The device is configured by a computer software to identify at least a pair of Noxipoints for applying one or more voltages to stimulate the Noxipoints.

25 Claims, 18 Drawing Sheets

# WEARABLE NOXIPOINTS STIMULATING DEVICES

CROSS-REFERENCE TO RELATED APPLICATION(S)

This application is a continuation-in-part application of the U.S. patent application Ser. No. 15/620,529, filed Jun. 12, 2017, and entitled "METHODS OF AND DEVICES FOR CHEMICAL AND THRESHOLD-GATED ELECTRICAL NEURO-IMMUNO-STIMULATION," which is a continuation application of the U.S. patent application Ser. No. 14/631,781, filed Feb. 25, 2015, which is issued as U.S. Pat. No. 9,713,543, and entitled "METHODS OF AND DEVICES FOR CHEMICAL AND THRESHOLD-GATED ELECTRICAL NEURO-IMMUNO-STIMULATION THAT TRIGGERS THE STEM CELL GROWTH TO RESTORE BODILY FUNCTIONS," which is a continuation-in-part application of the U.S. patent application Ser. No. 13/396,605, filed Feb. 15, 2012, which is issued as U.S. Pat. No. 9,205,256, and entitled "Nocipoint Therapy: Threshold-gated Electrical Neuro-Immuno-Stimulation Procedure," which claims priority from U.S. Provisional Patent Application Ser. No. 61/443,258, and titled "Threshold-gated Electrical Neuro-Immuno-Stimulation Procedure," filed Feb. 16, 2011, which are all hereby incorporated herein by reference in their entirety for all purposes.

Further, U.S. Provisional Patent Application Ser. No. 61/944,216, filed Feb. 25, 2014 and entitled "Pharmacologic and non-pharmacological Solutions that trigger the stem cell growth to restore bodily functions permanently," which is hereby incorporated herein by reference in its entirety for all purposes.

FIELD OF THE INVENTION

At least one embodiment of the present invention pertains to medical procedures and more particularly, but not exclusively, to reducing pain and restoring bodily function through electrical stimulation of Nocipoints.

BACKGROUND OF THE INVENTION

Chronic skeletal-muscular pain costs the US $200+B a year and increasing in terms of loss of time and medical expenses according to the 2011 CDC report. However, they are merely the manifestation of the underlying causes-skeletal-muscular injuries or pinched nerves.

Skeletal-muscular injuries from car accidents, sports, exercises, sudden movement, wrong postures or sometime unknown reasons are the major cause of such pain. Standard self-care process includes cold/heat pads and good rest for a period of time. In many cases, especially in acute cases, the body recovers; the muscle injury heals, and the pain disappears. Unfortunately, many people, 112 million in the US, get stuck with chronic pain, according to the CDC report.

Pinched nerves at spinal cord cause pain syndromes or loss of motor control at extremities (arms and legs). When a motor nerve is pinched, the patient experiences weak muscle response or even loss of motor control of the affected arm/leg. When a sensory nerve is pinched, the patient experiences tingling sensation, numbness in certain areas of the affected arm or leg. Herniated discs are often cited as the cause of the problem in radiological interpretation of CT scans. However, it is misleading because (1) most herniated discs do not even touch the nearby nerve and thus not necessarily cause any pain, and (2) herniated discs occur even in normal people with no pain or known injury. Most pinched nerve problems, as our clinical study indicates, are actually caused by injuries of the muscle groups that support and balance the spine. When the injuries of those corresponding muscles, mostly near the neck or the lower back, are healed, the pinched nerve problem and any associated pain disappear as well.

Standard treatments for chronic pain typically include physical therapy, pain medication, epidural injection of steroids, and surgeries. The treatment process is long and ineffective: Majority of the patients had little or no improvement after six months or longer of various therapies. The epidural injection is useful to reduce neural inflammation. However, most of the chronics pains described above are not neural inflammation. Thus, majority of patients either experience no improvement or temporary improvement with a rebound in a few days or few months when the epidural steroid wears off. In addition, due to the serious side-effect of steroids, epidural injection can only be used for several times. The prognosis of surgery was even less positive. Most of patients who undergo such invasive surgeries on and after six-month recovery periods found that their conditions are not better or even worse than before the surgery. Pain medications, including both prescription anti-inflammatory drugs and over-the-counter analgesic medicine, are often used to relieve the pain temporarily and reduce the inflammation hoping that the body will heal the injury itself once inflammation is reduced. For some patients with acute injury, the pain medication will bridge them through the recovery process with less or no pain. Unfortunately, chronic pain patients usually experience temporary relief with medications. The pain returns within hours after medication is taken. In essence, majority of people who have chronic pain would go through multiple years of treatments without a permanent cure.

Besides in muscular-skeletal conditions, pain is also associated with many internal medicine conditions. Based on extensive systematic review of medical and biological articles, when organ (such as muscle) tissues are injured (which can be inflicted by physical harm, disease, infection, degeneration, etc.), it can trigger a cascade of the healing process mediated by innate immune system: The injured muscle/soft tissue triggers the release of cytokines (chemicals carry signals to promote or inhibit immune responses), which recruit the innate immune cells (e.g., macrophages) to take away the dead and injured tissue cells or the scar tissues around them. Macrophages in turn release other cytokines (e.g., IGF-1, TNF-alpha, hepatocyte growth factor (HGF) and protease) and trigger the cascade of the muscle tissue repair and regeneration. In normal cases, the immune and regenerative process eventually heals the muscle. Unfortunately, the process often gets interrupted and never completes. Interruptive processes include:

Scar tissue formation (b-FGF→fibroblast→fibrosis→scars)

Excessive and prolonged inflammation

Sheared muscle (structural damage of the connective tissue/framework)

Age effect

Cycle aborted due to various environmental influences

When interrupted, the patient is stuck with the chronic pain and organ injury.

SUMMARY OF THE INVENTION

Our clinical study conducted in the application implicates that nociceptors (i.e., pain receptors) of the muscle sensory nerve (esp., the C-fiber) participate in the healing process and ensure the positive signaling to the healing process and that the specific threshold-gated electrical stimulation procedure described in this application triggers the neural signaling and thus the healing process on the immune system side, based on the thousands of cases in which muscle injuries/pains recovered within a few hours to a few days after the procedure.

In one aspect, the method comprises identifying a pair of Noxipoints, wherein the pair of In some embodiments, Noxipoints are located at two ends of a strain of organ (e.g., muscle) tissue/fiber and applying a predetermined electrical or chemical stimulation to the pair of Noxipoints (in the case of skeletal muscles, Noxipoints are mainly at the tendon near the attachments). In some other embodiments, the application a predetermined electrical or chemical stimulation to the pair of Noxipoints triggers a reaction of a neuroimmune cascade. In another embodiments, the chemical stimulation comprises nociceptive chemicals. In other embodiments, the nociceptive chemicals comprise capsaicin. In yet other embodiments, the chemical stimulation comprises substance P, TNF-α, growth factors such as Insulin-like Growth Factor I (IGF-1) and Hepatocyte Growth Factor (HGF), or a combination of Substance P, TNF-α and/or growth factors.

In other embodiments, the electrical stimulation comprises increasing an applying voltage until an occurrence of a soreness, an achiness, a dull pain, or a combination thereof. In some other embodiments, the method further comprises adjusting an intensity, a wave length, a train frequency, a wave pattern of the applied electrical stimulation until the occurrence of the soreness, the achiness, the dull pain, or the combination thereof. In some embodiments, the pair of Noxipoints is located at two attachment ends of a muscle group.

In other embodiments, the pair of Noxipoints are located at two opposite sides of an organ. Some muscles are short and spread throughout the organ (e.g., heart, stomach, kidney, liver, etc.), in which the Noxipoints are located throughout the organ. In some other embodiments, the applying a predetermined electrical or chemical stimulation to the pair of Noxipoints enhances a growth rate of one or more stem cells. In some embodiments, the applying a predetermined electrical or chemical stimulation to the pair of Noxipoints activates one or more satellite cells or other stem cells. In other embodiments, the applying a predetermined electrical or chemical stimulation to the pair of Noxipoints increases a rate of self-healing process.

In another aspect, a treatment device comprises a user-interface control panel configured to receive an input of a response of an applied electrical stimulation and an electrical control circuit configured to tune the applied electrical stimulation. In some embodiments, the response comprises feeling of a soreness, an achiness, a dull pain, or a combination thereof. In other embodiments, the electrical control circuit is configured to increase an applied voltage when an input is not a feeling of a soreness, an achiness, a dull pain, or a combination thereof. In some other embodiments, the device further comprises a software indicating a location of a corresponding Noxipoint of a pair of Noxipoints. In some other embodiments, the software comprising a 3D modeling of a human anatomy.

In another aspect, a method of enhancing a healing process comprises applying a predetermined stimulation on a pair of Noxipoints and enhancing a rate of healing by applying the predetermined stimulation. In some embodiments, the predetermined stimulation comprises an applied electrical stimulation until an occurrence of a soreness, an achiness, a dull pain, or a combination thereof. In other embodiments, the predetermined stimulation triggers a signaling pathway of a differentiation of one or more adult stem cells. In some other embodiments, the predetermined stimulation triggers the generation or release of an amount of substance P.

In some embodiments, the predetermined stimulation makes a mast cell release histamine and a cytokine. In other embodiments, the cytokine comprises a tumor necrosis factor-alpha (TNF-α). In other embodiments, the predetermined stimulation causes a macrophage to conduct phagocytosis on a scar tissue or an impaired tissue. In some embodiments, the predetermined stimulation comprises an external application of an amount of substance P, TNF-α, growth factors or a combination of substance P, TNF-α and growth factors. In some embodiments, the term "Nocipoint" is interchangeable with the term "Noxipoint".

In another aspect, a method of Noxipoint stimulation comprising forming multiple electrodes on a hosting member and coupling an electrical power source to the multiple electrodes. In some embodiments, the method further comprises identifying a pair of Noxipoints, wherein the pair of Noxipoints are located at two terminal ends of a muscle fiber and applying a predetermined electrical or chemical stimulation to the pair of Noxipoints.

In some embodiments, the method further comprises using an electrical control circuit configured to adjust a pulse pattern applied to the Noxipoints. In other embodiments, the electrical control circuit is configured to adjust a pulse duration applied to the Noxipoints. In some other embodiments, the electrical control circuit is configured to adjust a pulse strength applied to the Noxipoints. In some embodiments, the electrical control circuit is configured to generate an anatomic site specific stimulation. In other embodiments, the electrical control circuit is configured to generate an intensity and submodality-specific stimulation. In some other embodiments, the submodality comprises a moderate soreness, an achiness or a mild dull pain. In some embodiments, the Noxipoints are on an organ. In other embodiments, the electrical control circuit is configured to triggers a reaction of a neuroimmune cascade at the pair of Noxipoints. In some other embodiments, the method further comprises a user interface configured to adjust an electrical stimulation at the pair of Noxipoints. In some embodiments, multiple electrodes are structured to form a matrix of electrodes. In other embodiments, the multiple electrodes are configured to apply alternative phases of applied voltages. In some other embodiments, the hosting member is a wearable electronic device. In some embodiments, the method further comprises applying an electrical voltage to at least two preselected electrodes among the multiple electrodes, wherein the at least two preselected electrodes are determined to be at or near locations of Noxipoints.

In another aspect, an electrical treatment device comprising a hosting member having multiple electrodes, a user controlling device containing a user control panel, and an electrical control circuit coupled with the hosting member configured to adjust an applied electrical stimulation based on an input received at the user controlling device.

In some embodiments, the electrical control circuit is configured to apply a predetermined electrical power to the pair of Noxipoints. In other embodiments, the hosting member comprises a wearable electronic device. In some other embodiments, the wearable electronic device comprises a hat. In some embodiments, the wearable electronic device comprises pants, a boot, a cloth, or a combination thereof. In other embodiments, the multiple electrodes are structured in a grid.

In another aspect, a method of using a Noxipoint stimulation device comprises preparing a wearable electronic device containing multiple electrodes, coupling an electrical power source to the multiple electrodes, identifying a pair of Noxipoints, and applying a predetermined electrical or chemical stimulation to the pair of Noxipoints. In some embodiments, the pair of Noxipoints are located at two terminal ends of a muscle fiber. In other embodiments, the pair of Noxipoints are located at two terminal ends of an organ. In some other embodiments, the method further comprises a computer software configuring the device for the identifying the pair of Noxipoints.

There are three different types of muscles: skeletal, smooth and cardiac muscles. Their respective pain (or Noxipoints) may or may not directly manifest on the muscle body but on adjacent areas (such as visceral pains). In these cases, Noxipoints may be at the referral pain points.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION OF THE PREFERRED EMBODIMENT

Nocipoint Stimulation Therapy—A Threshold-Gated Electrical Neuro-Immuno-Stimulation:

The Nocipoint Stimulation Therapy is a process using electrical stimulation in a precise manner that activates the complete healing of (1) muscle injury with associated local pain, and (2) muscle injury that causes pinched nerve and indirectly causes remote pains and/or loss of motor control at the extremities (legs, arms) in a short time:

Steps:

(1) The patient identifies the general area of the pain: (e.g., the left shoulder/the lower left back)

(2) Decide whether the pain is caused by the muscle(s) locally or a pinched nerve at the spinal cord remotely. In the latter case, find the muscle groups that structurally support the vertebrae near the pinched nerve. A few tests are well documented in clinical diagnosis to differentiate local muscle pain from pain/muscle weakness caused by pinched nerve. To name a few:
  a. Injury history: If someone springs his/her ankle, the ankle pain is most likely caused by local injury.
  b. The local pains are usually associated with certain movement and will always present when the same movement is performed.
  c. The pain caused by pinched nerve often can be temporarily relieved by changing the patient's posture s or via spinal traction. These maneuvers can be used to differentiate the pinched nerve problems from local muscle injuries. However, the pain will come back soon afterward.

Figure 1:
FIG. 1 illustrates a 59 year old patient injured his back after trying to pick up a heavy box. Couldn't bend more than 20 degrees. Had lower back pain.

See FIG. 1. Example: A 59 year old patient injured his back after trying to pick up a heavy box. Couldn't bend more than 20 degrees. Had lower back pain.

(3) Use the human anatomy to locate the muscle(s) that is likely to be responsible for the identified pain area above. This research has found that the anatomical layout of each muscle and its expected kinetics is critical in identifying the muscle. A 3-D anatomy model will be useful for this.

Figure 2:
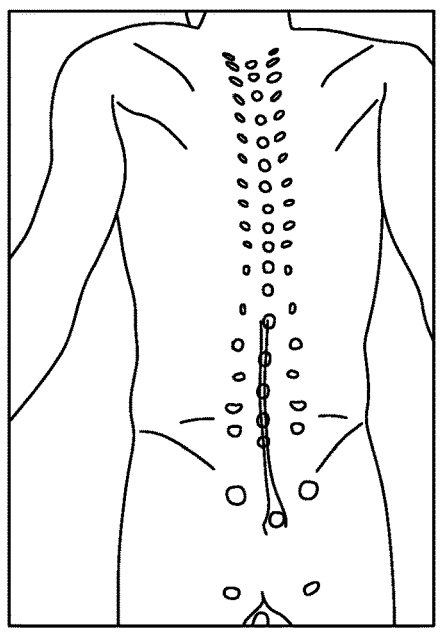
FIG. 2 illustrates locating muscle group(s) responsible for the pain of the example patient.

See FIG. 2. Locate muscle group(s) responsible for the pain.

(4) Find the first "Nocipoint": Based on the candidate muscle group(s) identified above, press at or near one of the insertion points of the muscle(s), and find the "Nocipoint". This research has discovered that a "Nocipoint" is a small area located at the end of an injured muscle tissue and is painful only when pressed/touched. These Nocipoints are very sensitive to even light presses, but patients usually did not feel any pain there if not so touched. The patient will experience sharp/noticeable pain when the Nocipoint is touched. Anatomically, they are where the nociceptors of the muscular sensory nerve (i.e., the free nerve endings) are.

Figure 3:
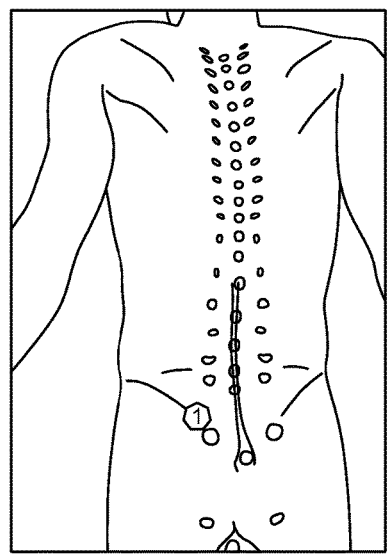
FIG. 3 illustrates an example of locating a "Nocipoint."

See FIG. 3. Example: Locate a "Nocipoint".

(5) Find the second matching "Nocipoint" by tracing the muscle in anatomy map: For each muscular injury/pain, one will ALWAYS find another "Nocipoint" near another insertion point at the other end of the muscle. Certain muscle groups with more than two insertion points will have multiple corresponding Nocipoints at the group level. Patients are often surprised by the presence of these pressure-induced pain points. Sometimes one of the Nocipoints is far away from the perceived painful area. Thus, following the muscle anatomically is critical to precisely locate the matching Nocipoints. Note that, while there may be more than two insertion points/ends of a muscle group (e.g., triceps), there are always exactly two ends of at the muscle fiber level, and thus two Noxipoints per muscle fiber. In other muscle groups (e.g., smooth muscle, cardiac muscle), Noxipoints are evenly distributed among the injured area of the organ, as the muscle cell in these types of muscle groups are typically short, and thus the two ends of the Nocipoints are very close to each other. In the case of brain, Nocipoints are outside of the skull around the head due to referral pain extended from the damaged neurons.

Figure 4:
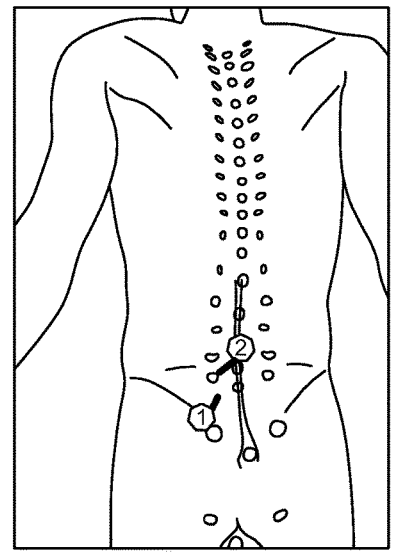
FIG. 4 illustrates tracing anatomically to find the second Nocipoint.

See FIG. 4. Trace anatomically to find the second Nocipoint.

The Nocipoints described here always come in pairs. No prior art has ever figured out that it requires a PAIR of the matching painful points per muscle group to induce the injury curing process.

The complexity comes in when multiple groups of muscles in the same area are injured. In such cases, multiple Nocipoints (sometimes as many as 4-6 points) may express in the nearby area and should be paired respectively based on the muscle anatomy.

(6) Noxipoint Stimulation Therapy: In order to trigger the responses of the C-fiber nerve nociceptors, the electrical stimulation at the neuron needs to fall within a narrow range in order to activating the neuro-immune cascade and gain the optimal curing effect. The signaling process of the sensory nerve has the following thresholds subcutaneously:

a. The firing threshold (when the depolarization of the neuron cell starts): around +/−10 mV at the neuron
b. The action potential (when the depolarization ends and repolarization of the neuron cell starts): around +/−60 mV at the neuron.
Based on the biofeedback of the patients in this study, it is evident that the electrical stimulation needs to be between the two thresholds to have curing effect. However, due to the high resistance (100K to 1.3M Ohm), the stimulating pulse at the skin surface degrades quickly before it reaches the free nerve ending (neurons) of the nocireceptor. It needs to be at much higher voltage/amplitude than what is measured at the neuron. Some clinical examples of the operating stimulations at skin surface (i.e., transcutaneous electrical nerve stimulation, TENS) are as follows:

| Wave pattern | Pulse frequency | Operating range of pulse amplitude |
| --- | --- | --- |
| Square wave/Sine wave | 9 Hz | 130 V-170 V |
| Square wave | 20 Hz | 70 V-95 V |

Note that the two transcutaneous stimulation patterns above match with the known behaviors of the spatial and temporal summation of the action potential at the sensory nerves, and typically needs a train of impulses. While the first pulse pattern has higher amplitude range, recruiting enough nerve endings to propagate the pain-signal; the second pattern works just as effective with a faster pulse (20 Hz vs. 8 Hz) yet lower amplitudes. There are numerous combinations of (frequency, intensity) pair to induce successful effect; but one of the important factors includes C-fiber-like sensation (soreness, achiness, sense of fatigue, dull pain, etc.)

Given that every person varies in age and sensitivity to pain, minor adjustments are needed sometimes: Further adjust the strength/frequency/wave pattern above the "firing potential" and within the "depolarization" range of the nociceptor. In certain embodiments, the working frequency range can be as high as about 70 Hz.

A simple biofeedback can be used to "calibrate" the stimulation setting: when the patient starts to feel a sensation of deep pressure-induced-dull-pain (i.e., when C fibers of the sensory nerve are triggered), but not a muscle spasm or sharper pain, the nociceptor is by definition above the firing potential and below the action potential thresholds. It is known that the C-fiber transmits "dull pain" or "soreness" signals (instead of the sharp pain). Thus, the patient-provided biofeedback of feeling the dull pain confirms that the electrical stimulation is within the above thresholds. That is the operating range of the Nocipoint stimulation. It is often more than once (up to three or 3.5 times) the intensity of activating the motor nerve in the area.

Note that all values above and below are approximate.

(7) For each pair of Nocipoints, carefully control the stimulation duration within a tight range between 1 minutes to 15 minutes. Minor variance is alright based on age and muscle tone, but excessive long time does not necessarily yield the best healing result.

(8) Repeat the process on other muscle if necessary: If the correct pair of Nocipoints is stimulated, the patient will experience instant relief of pain of the stimulated muscle. And within a few minutes, the muscular function starts to heal and recover. Typically, however, multiple muscle injuries collectively cause the pain. Thus, repeat the same process to all other pairs of the Nocipoints.

Figure 5:
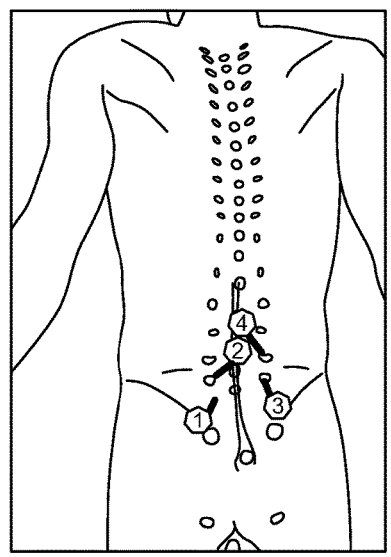
FIG. 5 illustrates an example case repeating the procedure on other pairs of Nocipoints.

See FIG. 5. Example case: Repeat the procedure on other pairs of Nocipoints.

(9) When all pairs of Nocipoints for the injured muscle groups are identified anatomically and stimulated, the process is complete. Pains will be relieved and patient will be able to regain functions after several days (during which the cells are remodeled). Typically, it will be completed within 2-8 hours in 1-5 sessions.

Figure 6:
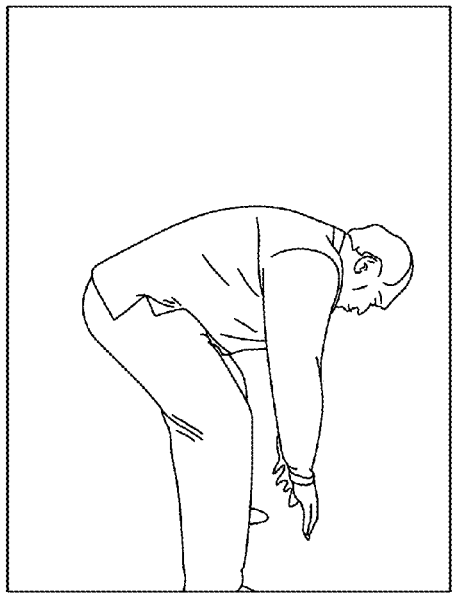
FIG. 6 illustrates within 25 minutes, the patient recovered after the first treatment with full motion range. No more back pain since then.

See FIG. 6. Within a couple of hours, the healing process starts, and eventually functional recovery occurs.

(10) Resting period: Immediately after the treatment is complete, the patient should go easy on the just-recovered muscles. These muscles take several days to heal and the tissues/fibers may not be strong enough after initial healing. To prevent new injury to the same muscle, wait for several days. For people who are aged or weak muscles, avoid extraneous uses for at least about one week. For young people or people with strong muscle tone, about 3-4 days of resting (of the treated tissue) are advised. During the resting period, some light exercise can be performed to train the newly healed muscles.

Control Study

1. Patient Profiles:
(a) Pain/tingling sensation at extremities or loss of motor control due to pinched nerves, which may or may not be present all the time. Most of them had functional deficiencies. Ages: 35-65
(b) Chronic neck pain and back pain for various (sometimes unknown) reasons, having lasted 2-20 years. All had tried many treatment protocols (physical therapy, epidural injection, acupuncture, massage, etc.) without notable improvement. Many were also on prescribed analgesics. Patients' ages are between 30 and 79.

(c) Lingering pain at extremities due to sports injuries, car accidents, or sudden movements. Many were functionally impaired for over 3 months (some multiple years). The age group: 15-68

(a) and (b) groups often had multiple areas of pain while Group (c) often had localized pain. Most of them experienced functional constraints of their arms, legs or the back. Many had symptoms from both tissue injury and pinched nerve. They were classified in either (a) or (b) for convenience. Many felt depressed, some showed allodynia or hyperalgersia. In general, these patients were all stuck with chronic pains and impaired muscular functions for a long time.

The Treatment Procedure:

The patients were given the Nocipoint Therapy: Electrically stimulate certain stimulation points that were anatomically relevant to injured tissues/sites with controlled timing, strength, dosing, etc. Because most patients had multiple problem areas, each session typically lasted for 1.5 hours.

The results (based on a study of 64 chronic pain patients):

100% patients recovered with full range of motion and only less than 10% reports Level 1 or 2 out of 10 remaining pain. 89% of patients recovered in 1-4 sessions. Full recovery is defined as (1) gaining full range of motion (age appropriate) and (2) persisting function for at least one month without recurring pains.

| Recovered in # of sessions | # of patients | percentage | Remaining pain (x/10) level when treatment stopped |
|---|---|---|---|
| 1 | 7 | 10.9% | 0-1 |
| 2 | 16 | 25.0% | 0-not noticable |
| 3 | 19 | 29.7% | 0-not noticable |
| 4 | 15 | 23.4% | not noticable-1 |
| 5+ | 7 | 10.9% | 1-2 ** |
| | 64 total | | |

Most patients experienced substantial or complete recovery of muscle function in the first one or two treatments. Later sessions were typically dealing with secondary/other pains that were not in the patients' chief complaint initially. (That is, when the primary problem is cured, the patient's perception starts to notice secondary and other pains.)

Arm and hand pains typically involve more muscle groups and often take longer time than neck/lower back pains.

** People who had extensive tissue damages required multiple sessions/more time to cover all the damaged tissues/muscle groups. Some patients who went through 4 or 5+ sessions stopped coming because they were happy with the substantial improvements.

Control-Test Analysis

Chronic pain patients typically have persistent pain for months or years, with other conventional treatment/therapy (See FIG. 1). The patients who received the Nocipoint Therapy experienced substantial pain relief and regained function immediately after the treatment. Unlike all prior arts, the recovery persisted. The control in this study is the historical pain level before the treatment, while the test is the pain level afterward the treatment (in the AFTER scenario).

Figure 7:
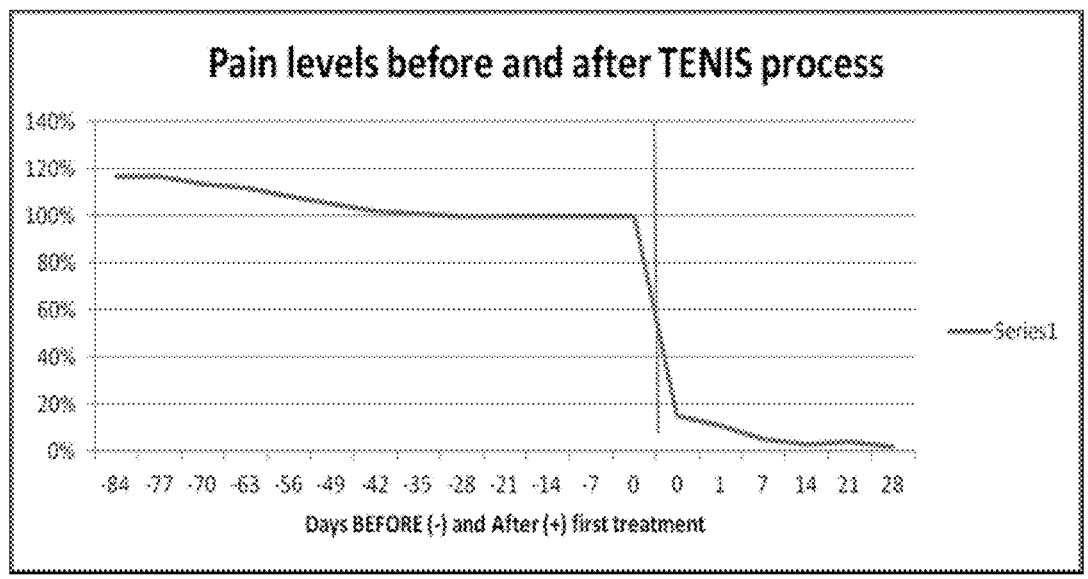
FIG. 7 is a chart illustrating relative pain levels BEFORE and AFTER the Nocipoint Therapy.

See FIG. 7. Relative pain levels BEFORE and AFTER the Nocipoint Therapy.

In order to have a meaningful aggregation across all patients, the pain levels are normalized at the time right before the treatment. That is, they are defined as relative pain compared to the pain level right before the Nocipoint Therapy. Chronic pain patients typically have persistent pain for months or years, with or without conventional treatment/therapy, as indicated in the BEFORE scenario. Patients who received the Nocipoint Therapy experienced substantial pain relief and regained function soon after the treatment (the AFTER scenario). Notice that the recovery persisted afterward. (Note: history earlier than 84 days before the treatment were ignored in this chart.)

Observations:

All treatments were done within one to several hours accumulatively, spreading over one or a few sessions. The gap between sessions has minor impact on recovery, positive or negative. That is, patients technically can complete all sessions consecutively in a short period.

Patients usually experienced immediate improvement/cure when the correct Nocipoints are stimulated. This contrasts the 1-2 years of standard pain management protocol. The Nocipoint Therapy is precise, reproducible, and with near-perfect success rate.

Elimination of the placebo effect: During a session, if the points for stimulation were off by a little from the intended points mistakenly (e.g., by ½ inch), or by a lot intentionally, the patient could tell and would instantly indicate the lack of improvement. Correcting the stimulation location to the right Nocipoints will enable instant result.

After each session, the patients were instructed to go easy on exercises with the newly recovered muscles for a few days or a week for seniors, to prevent new injuries before the tissue gains enough strength.

In sum, the procedure cures pains permanently and persistently. More importantly, it heals injured tissues and restores functions. It is repeatable and the same results occur in nearly all cases.

A Recent Example: (with Patient's Permission):

The patient is 59, who injured his lower back a week before the treatment while picking up a heavy box. Had been in pain and had to roll off the bed every day. Worn waist support all days to avoid pain.

Figure 8:
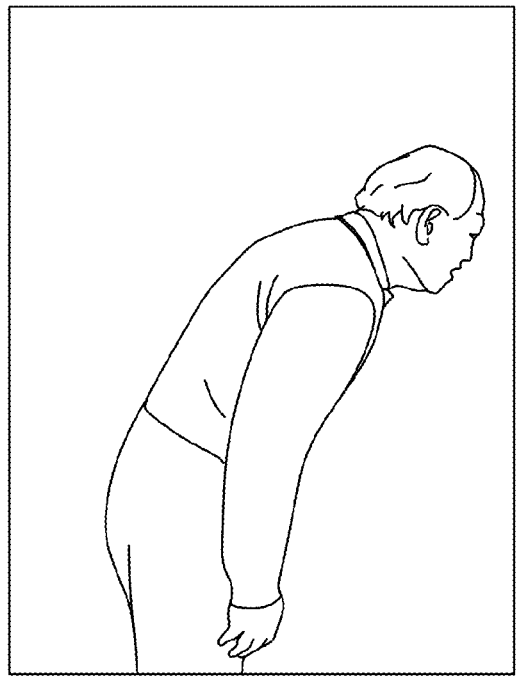
FIG. 8 illustrates a patient before treatment.

Before the treatment: See FIG. 8: the maximum angle he could bend without waist support)

Figure 9:
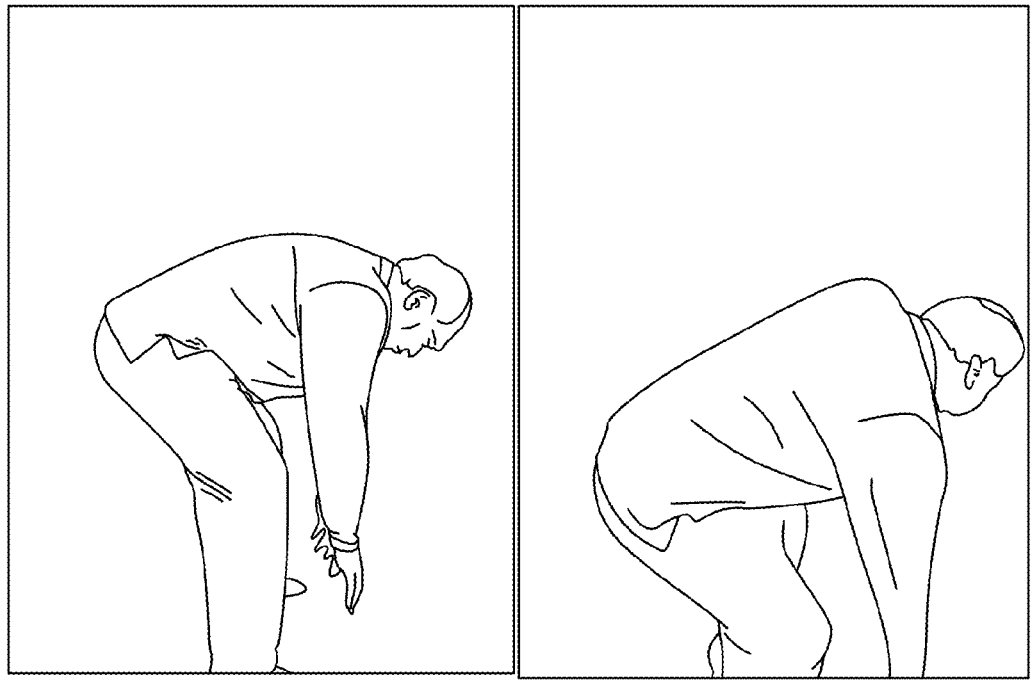
FIG. 9 illustrates the patient after treatment.

After a 25-minute treatment: Full range of motion recovered. No pain since. See FIG. 9.

Note that any and all of the embodiments described above can be combined with each other, except to the extent that it may be stated otherwise above or to the extent that any such embodiments might be mutually exclusive in function and/or structure.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

Pharmacologic and Non-Pharmacological Solutions that Trigger the Stem Cell Growth to Restore Bodily Functions Permanently In the following, methods of and devices for permanently restoring bodily functions using pharmacologic and non-pharmacolgic solutions are disclosed. In some embodiments, the present invention is used to treat/cure the underlying causes, symptoms (often manifested as pains).

Figure 10:
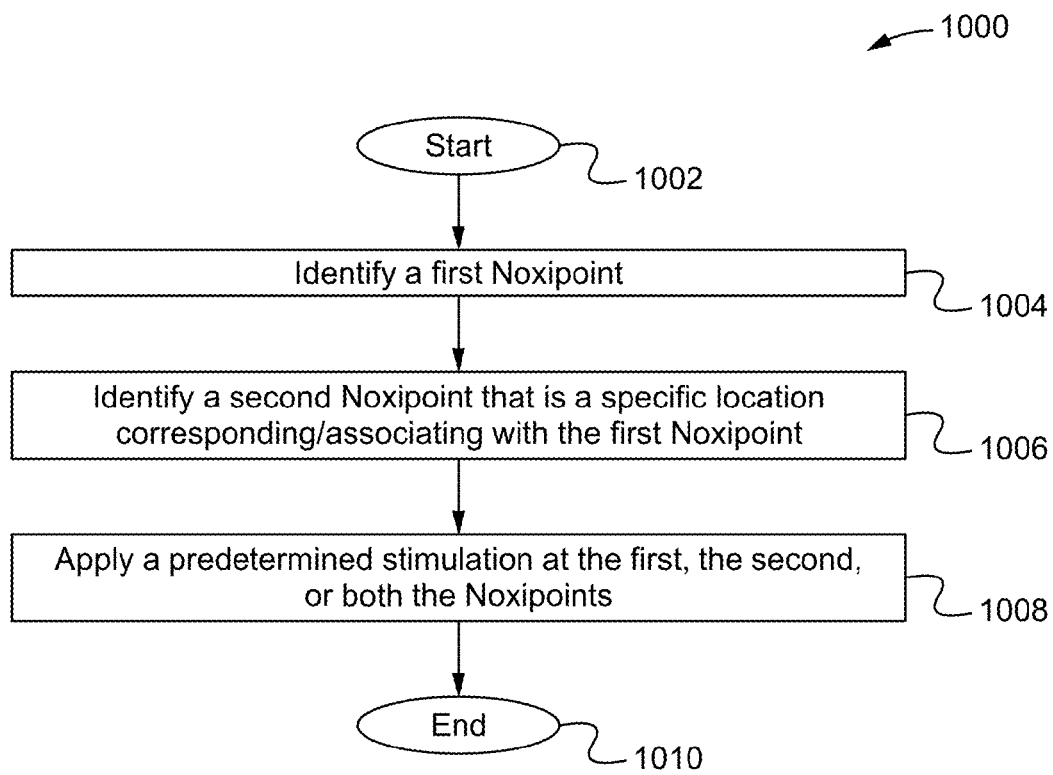
FIG. 10 is a flow chart illustrating a restoring bodily function method in accordance with some embodiments.

FIG. 10 is a flow chart illustrating a restoring bodily function method 1000 in accordance with some embodiments of the present invention.

The method 1000 can start at Step 1002. At Step 1004, a first Noxipoint is identified. In some embodiments, the Step 1004 is performed by identifying a general pain area, which is able to be done by a patient, a sensing device, or a medical professional, palpating the organ (e.g., in the case of muscle, at attachment points (origin and insertion) of each muscle group and soft tissue) within or near the pain area, and identifying a set of pain points sensitive to pressure (e.g., Noxipoint).

At Step 1006, a second Noxipoint that is a specific location corresponding/associating with the first Noxipoint is identified. In some embodiments, the Step 1006 is performed by locating a corresponding tissue cluster (e.g., a muscle group or soft tissue) as a target of stimulation applying point. The first and the second Noxipoints generally appear on both of the tissue cluster attachments (e.g., at the two terminal points of a strand of a muscle fiber). Noxipoints are generally existing in pairs. For example, a second corresponding Noxipoint can be located when a first Noxipoint is located. Further, a second set of plural Noxipoints can be found when a first set of plural Noxipoints are found. The first set and the second set of the Noxipoints are generally located at two terminal ends/points of a group of muscle fibers.

At Step 1008, a predetermined stimulation is applied at the first, the second, or both of the Noxipoints. In some embodiments, the predetermined stimulation comprises a physical stimulation, a chemical stimulation, or a combination thereof, such as a chemical induced physical stimulation or a physically induced chemical/physiological response. For example, the physical stimulation comprises an applied electrical power/voltage stimulation and the chemical stimulation comprises an applied chemical stimulation, such as injection of a predetermined amount of chemical substances.

In some embodiments, chemical stimulations (such as nociceptive chemicals; e.g., capsaicin) are applied at the precise spot of the Noxipoints of the target muscle/tissue cluster identified in Steps 1004 and 1006 via injection or by using a cutaneous patch. In some embodiments, substance P, TNF-α, or a combination of TNF-α and growth factors (such as IGF-1) are applied at the precise spots of the Noxipoints. Nociceptive chemicals, substance P, TNF-α, and/or a combination of TNF-α and growth factors are able to be applied at the same time at the target muscle/soft tissue. The applications are able to be used at multiple sites simultaneously.

In some embodiments, straining treated areas are avoided during a "resting period" after each treatment and braces are used in moderate or severe cases. Patient is advised not use or strain the newly treated muscle/tissue during the "resting period" for 1-10 days or a minimum of three days. If the patient has extensively impaired muscles, they are advised to take two more days of resting. The method 1000 can stop at Step 1010.

Figure 11A:
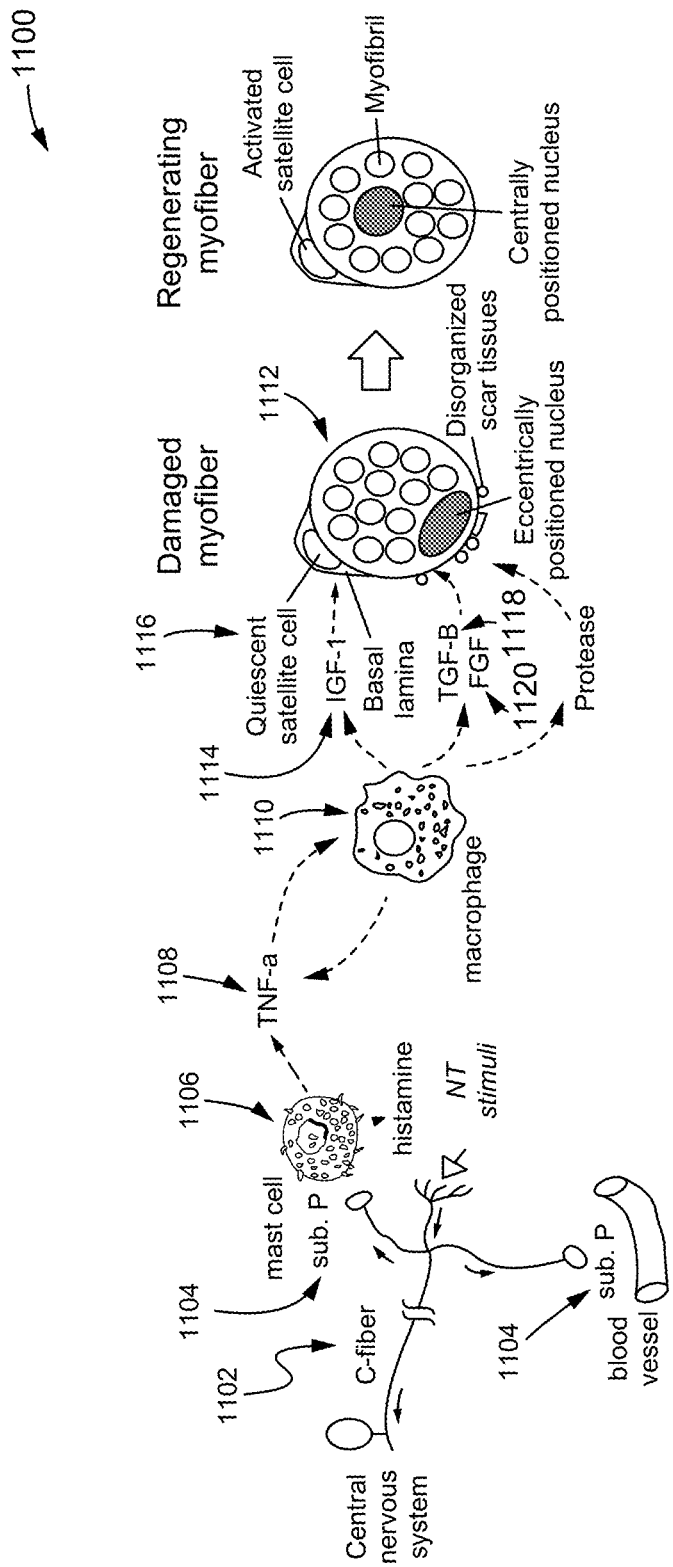
FIG. 11A illustrates a method that restores impaired bodily functions via the division and proliferation of progenitor stem cells in accordance with some embodiments.

FIG. 11A illustrates a method 1100 that restores impaired body functions via the division and proliferation of progenitor stem cells in accordance with some embodiments of the present invention.

The method 1100 illustrates an induced cellular signaling pathway that activates the mechanisms for repairing and regenerating organ/tissue cells. The stimulation on the Noxipoints causes the C-fiber nociceptor 1102 to emit substance P 1104, which in turn triggers the mast cell (MC) 1106 or other immune cells on site to release histamine and TNF-α 1108. TNF-α 1108 recruits the macrophage 1110 locally to conduct phagocytosis on scar tissues/impaired cells 1112 and to release growth factors 1114 (such as IGF-1) that activate the differentiation of progenitor stem cells 1116 (such as myo-satellite cells) in the neighborhood, which in turn repair the impaired muscle/tissue. Other growth factors produced by the macrophage that are myogenic for satellite cells include transforming growth factor-beta (TGF-β) 1118 and basic fibroblast growth factor (FGF) 1120, which promote chemotaxis of satellite cells 1116 in the tissue toward the impaired site. Macrophages release additional TNF-α 1108 locally that recruits more macrophages, further expediting the process. In addition, Sub P 1104 or other downstream cytokine/growth factor in this signaling pathway promotes angiogenesis besides myogenesis mediated by satellite cell proliferation and division. In some embodiments, an amount of substance P, TNF-α, or a combination of TNF-α and growth factors are able to be applied on the Noxipoint to trigger/enhance the signaling pathway as described above.

Figure 11B:
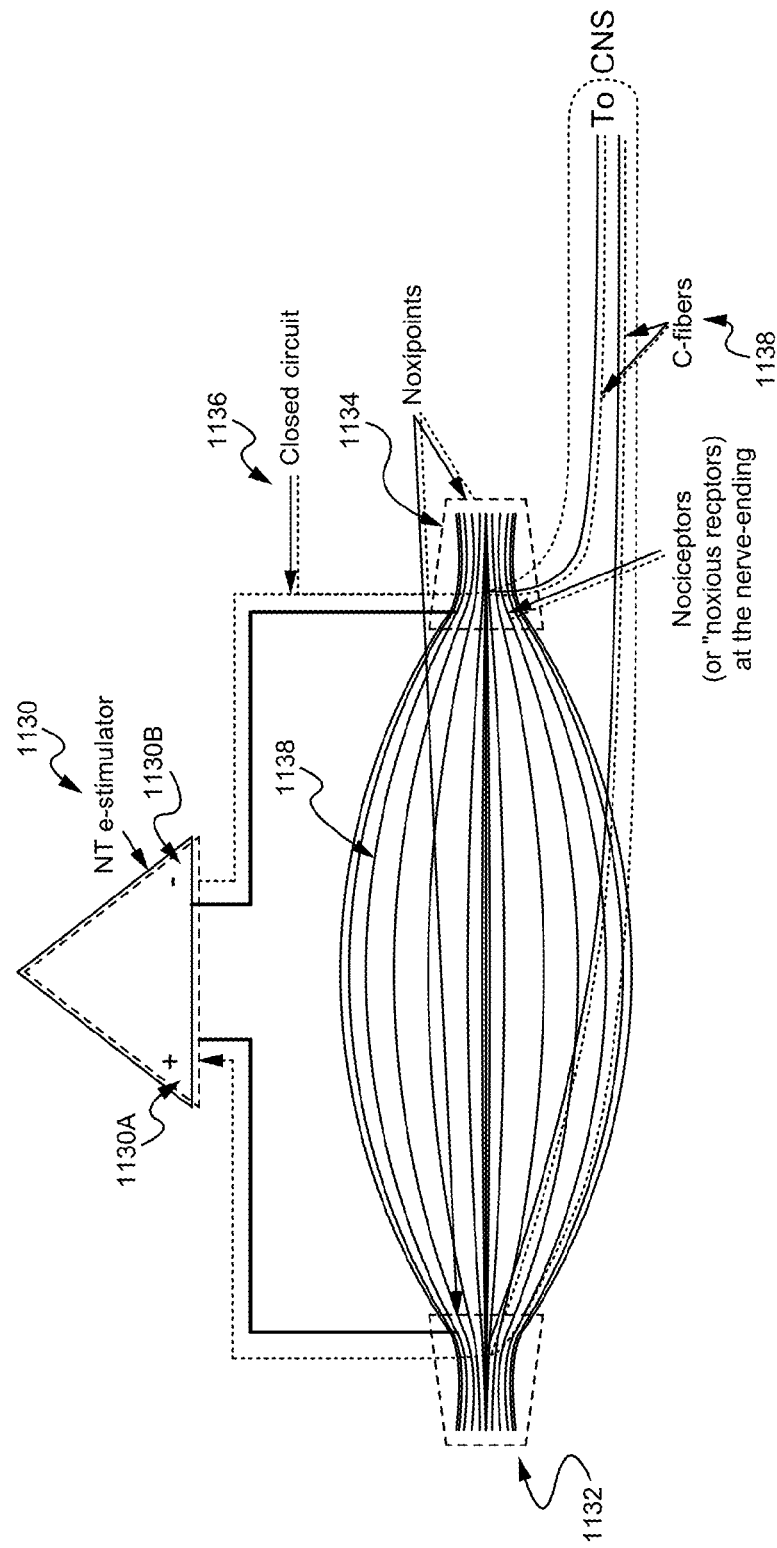
FIG. 11B illustrates an electrical potential applied noxipoint therapy process in accordance with some embodiments.

FIG. 11B illustrates an electrical potential applied Noxipoint therapy process in accordance with some embodiments of the present invention. A Noxipoint stimulation device 1130 comprises a positive terminal 1130A and a negative terminal 1130B. The positive terminal 1130A couples with a first applying point 1132 and the negative terminal 1130B couples with a second applying point 1134. The first and the second applying points are located at the two terminal ends of a muscle fiber 1138. The positive terminal 1130A, the first applying point 1132, the second applying point 1134, and the negative terminal 1130B form a closed electrical circuit loop 1136. In some embodiments, the first applying point and the second applying point form a pair of Noxipoints, which couple with c-fibers 1138.

Figure 11C:
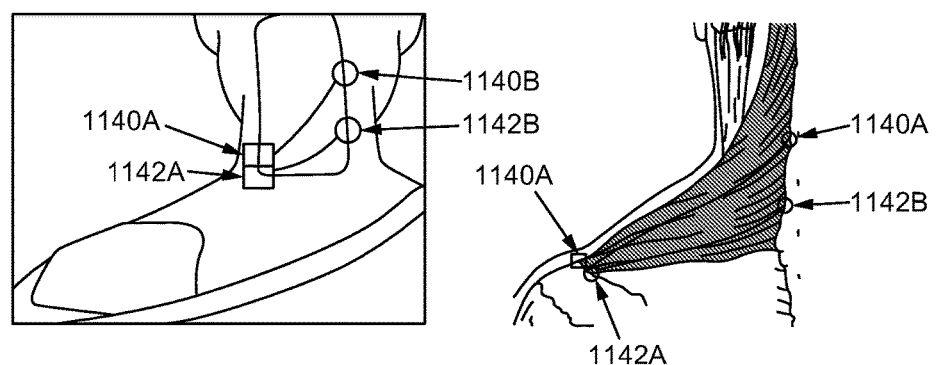
FIG. 11C illustrates a noxipoint therapy on an upper part of the impaired trapezius in accordance with some embodiments.

FIG. 11C illustrates a Noxipoint therapy on an upper part of the impaired trapezius in accordance with some embodiments of the present invention. A first Noxipoint 1140A has a corresponding second Noxipoint 1140B, where the first and the second Noxipoints are located at two terminal ends of a muscle fiber Similarly, a first noxipoint 1142A has a corresponding second noxipoint 1142B.

FIGS. 12A-12D illustrate a Noxipoint stimulating device 1200 in accordance with some embodiments of the present invention. The device comprises a display with buttons 1202 (e.g., on a GUI-Graphical User Interface), each of which represent a sensation, and a mechanism to depress the buttons (e.g., mouse, touch screen, or voice command), an electrical stimulator 1204 with a range of controllable parameters including voltage, wave pattern, train frequency, timer, and a communicating/control mechanism 1206 with a programming interface. The device 1200 comprises a pair of electrical pads 1208, such that the device 1200 is able to generate electrical pulses on a user.

In some embodiments, the display with buttons 1202 comprises various user interfaces, such as a dial type 1202A (FIG. 12B), which allows a user to increase/decrease an applying voltage by turning the dial. In some embodiments, a graphical user interface (GUI) 1202B provides a selection menu allowing a selection of patient's feelings. By selecting a pre-set feeling, the device 1200 is able to adjust its applied pulse, duration, strength, among other factors. A person of ordinary skill in the art appreciates that the user interfaces are able to be adjusted and programmable. For example, each possible sensory response to the electrical stimulation is indicated as a button on the control panel. Each such button corresponds to a different predetermined increment/decrement of the parameters of the electrical stimulation in the Noxipoint device. When the user presses a button, the corresponding change is performed continuously. When nothing is pressed, it maintains the same setting. The zone 1202C indicates the terminal state. When any of the buttons 1202D is pressed, the setting of the Noxipoint stimulation device is fixated or the change substantially slowed down until further instructed.

Figure 12A:
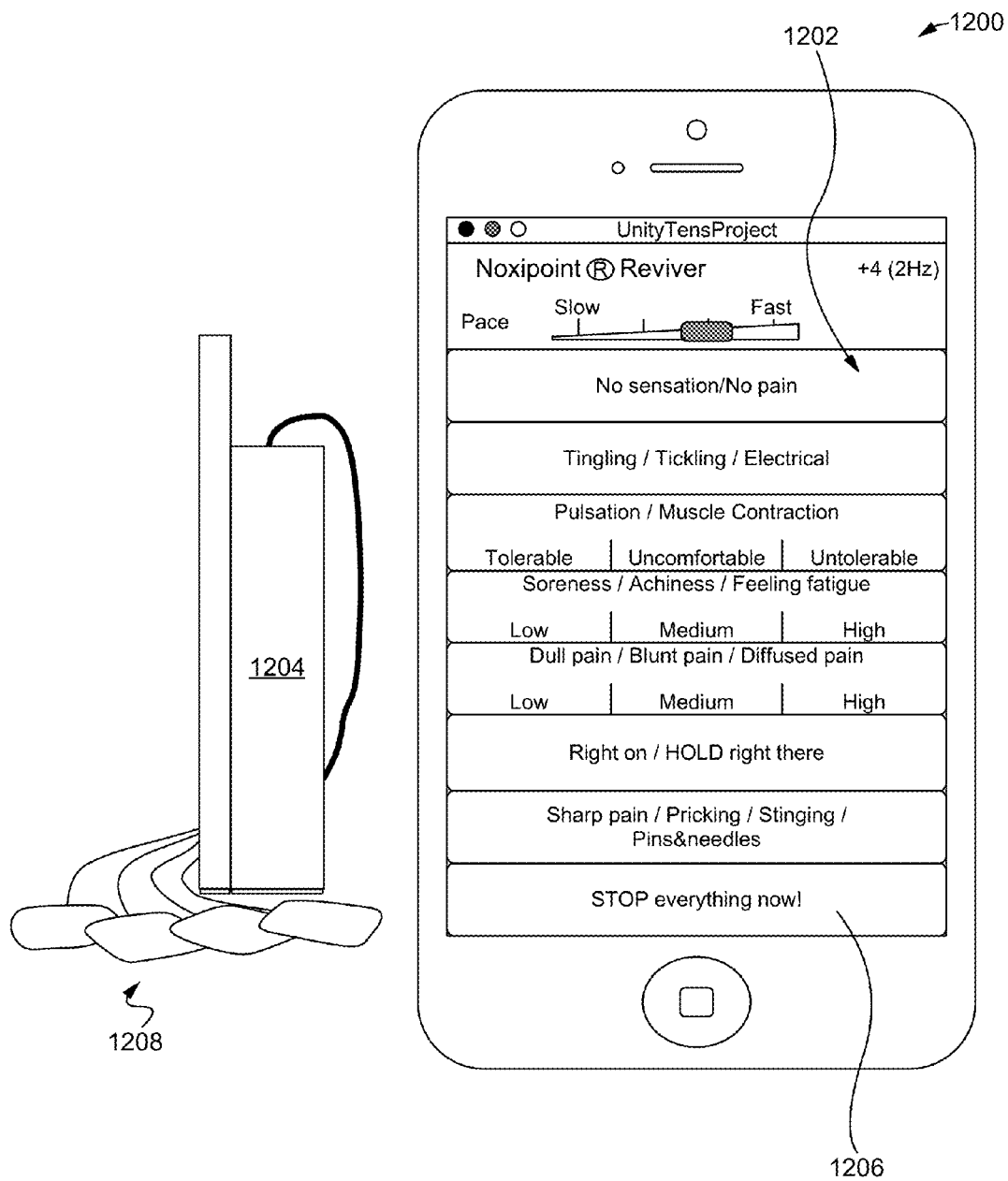
FIGS. 12A-12E illustrate a noxipoint stimulating device and method of using the device in accordance with some embodiments.
Figure 12B:
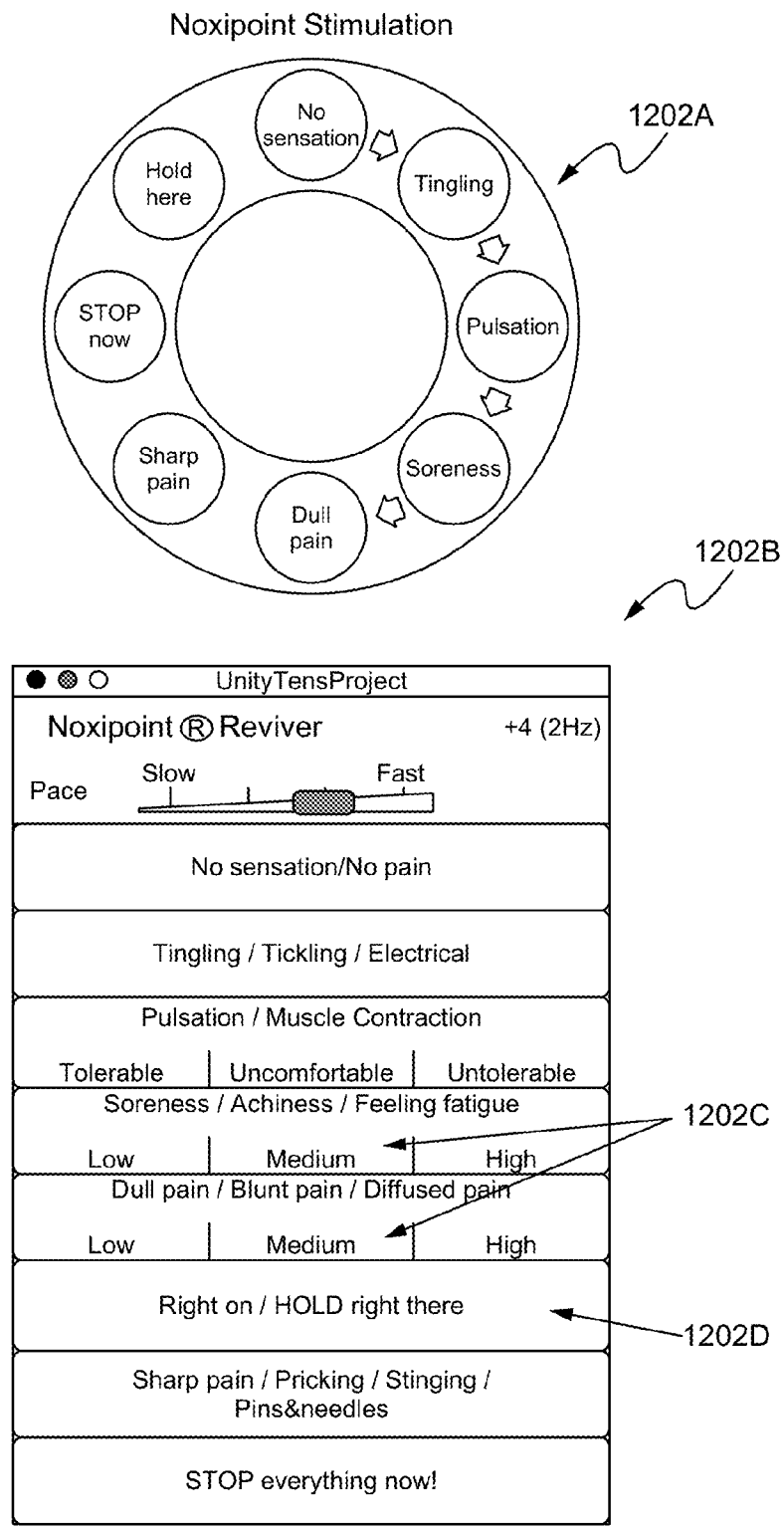
Figure 12C:
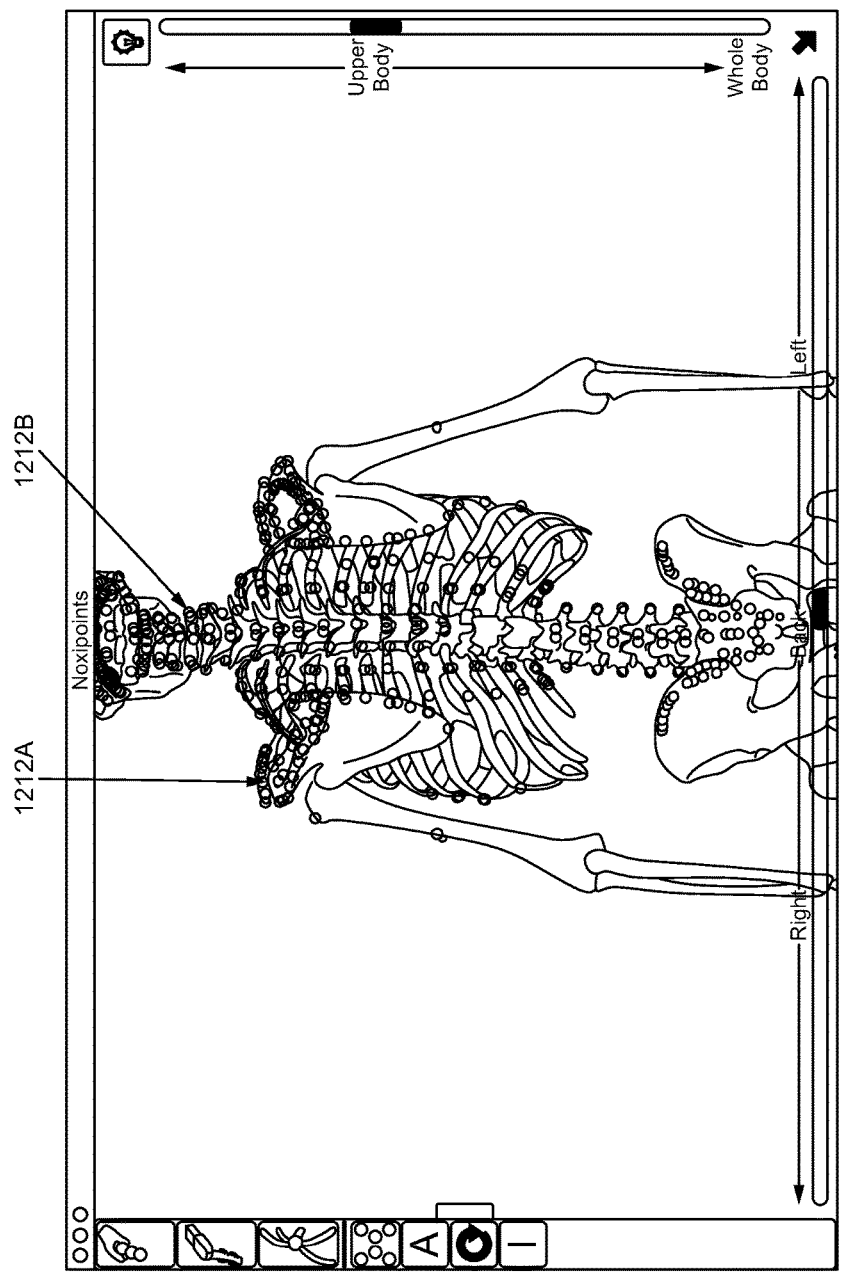
Figure 12D:
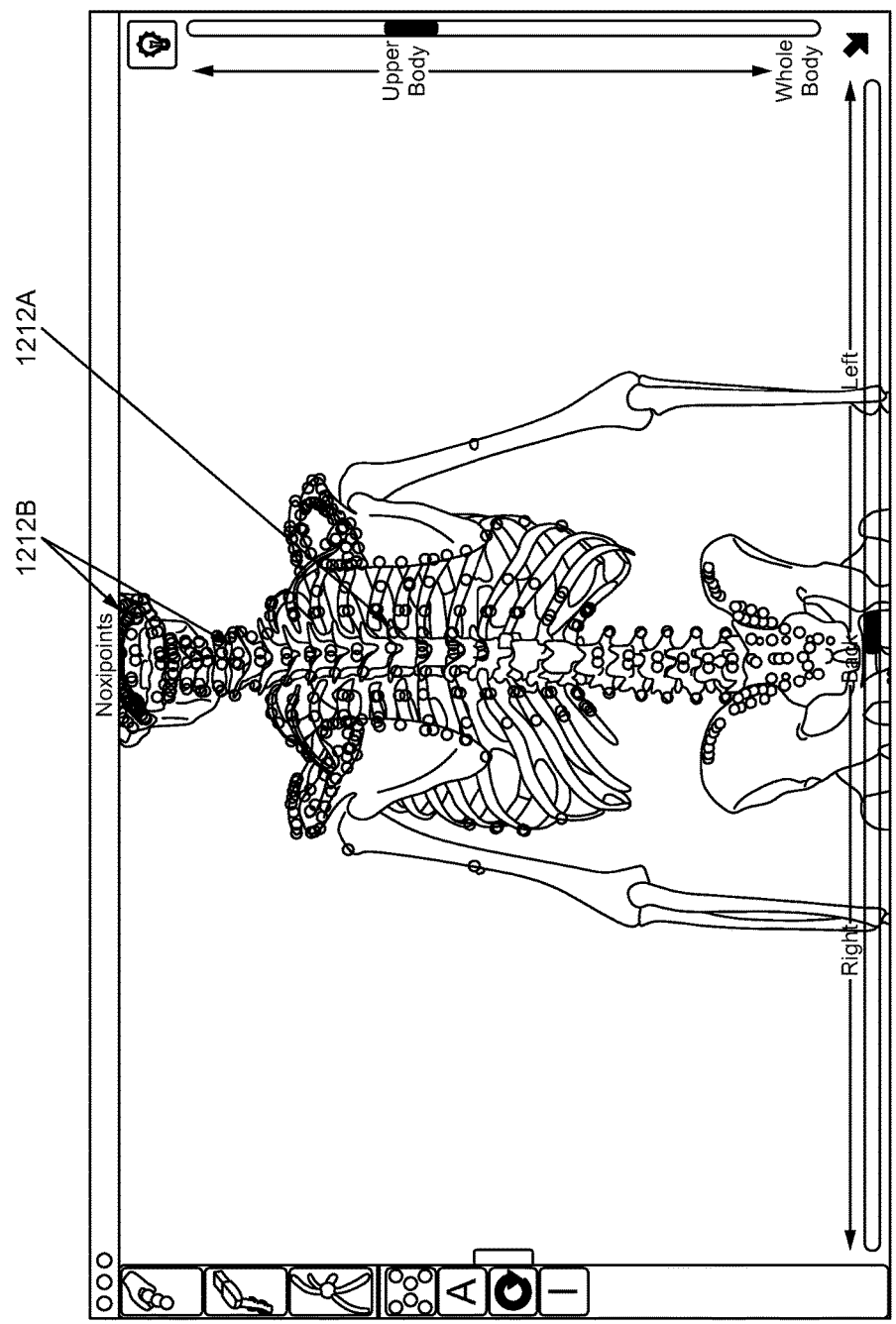

In some embodiments, the device 1200 comprises a 3D modeling software (Noxipoint Navigation system) as shown in the FIGS. 12C and 12D, which show the locations of the corresponding Noxipoints based on the human anatomy. For example, when a first Noxipoint 1212A is selected due to the patent's expression of pain and soreness, the corresponding Noxipoint 1212B is identified by the software system of the present invention, such that an application of a stimulation on the second Noxipoint can be performed.

In the following, a Noxipoint process (NP) performed using the device 1200 is illustrated in accordance with some embodiments of the present invention. The device 1200 is able to perform unique stimuli with one or more of the following characteristics: anatomic-site-specific stimulation (at corresponding Noxipoints of each target tissue), intensity-and-submodality-specific setting (eliciting soreness or dull pain but not sharp pain) and brief duration of the stimulation.

The process is able to be performed as follows:

(1) based on the general pain area identified by the patient, palpate the organ (e.g., at attachment points (origin and insertion) of each muscle group and soft tissue in the case of skeletomuscular cell; or where the nociceptors of the organ are) within or near the pain area, and identify a set of pain points sensitive to pressure (e.g., Noxipoint). A cluster of myocells or soft tissue cells is identified as a target when Noxipoints appear on both of its two ends;

(2) the stimulation pads/needles are precisely placed at the locations of the pair of Noxipoints corresponding to the impaired target muscle/tissue (the target) identified in (1) for about 4-5 minutes per application. For internal organs, stimulation pads/needles are placed at most painful pairs of the identified Noxipoints. After each application, a new pair of target Noxipoints is identified for the next pad/needle placement and application. Multiple pairs of Noxipoints are able to be stimulated at the same time;

(3) the stimulation is set to induce the specific nociceptive submodality of moderate soreness, achiness or mild dull pain (which is the signature sensation of the C-fiber nociceptor) based on the patient's confirmation during the application. Intensity, wave length, frequency and wave pattern/mode are adjusted collectively to achieve such sensation.

In some embodiments, the setting to achieve such sensation for each muscle group (e.g., deltoid) is not a constant but varies greatly from person to person (e.g., 92V, 300 µsec train-length, 2 Hz or Burst mode vs. 55V, 50 µsec train-length, 3 Hz, Burst mode).

Figure 12E:
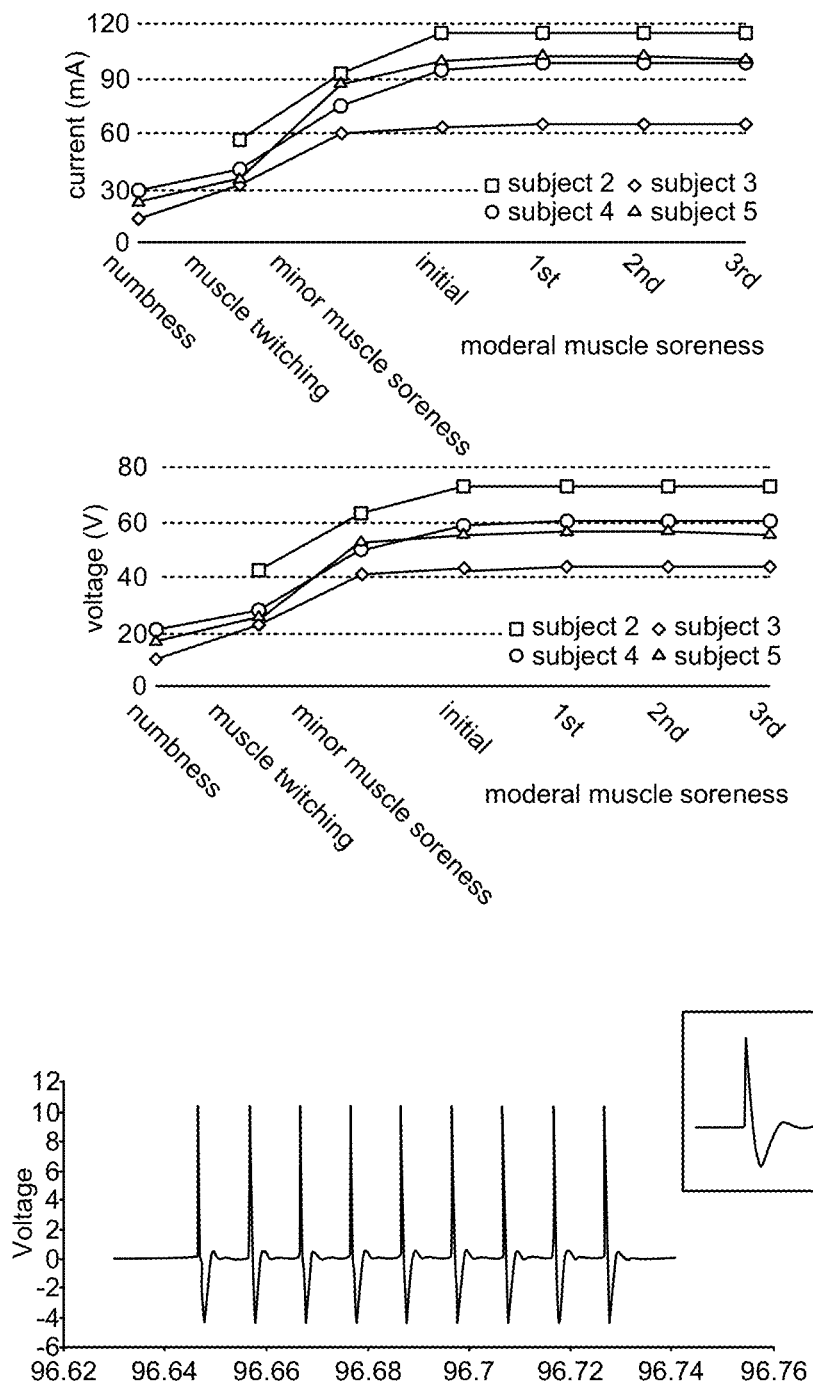

As shown in FIG. 12E, the settings to reach the target state (sorness/achiness/mild dull pain) in an example application to a particular muscle (e.g., gastrocnemius) among several subjects vary widely. The setting/controlling parameters include applied wave type, the frequency, and the pulse. In some embodiments, the therapist/user used the device 1200 to reach the soreness/dull pain state smoothly in the stimulation process.

In some embodiments, the device 1200 comprises a touch screen computer/smart phone device interfaced/integrated with an electrical stimulator. In some embodiments, the process disclosed herein can be enhanced by combining the steps in the above mentioned drug and device processes. By providing drug at or near the target site to be treated and stimulating the impaired tissue (organ), the integrated process delivers the drug precisely at the site where the drug is needed with stronger doses than what the body naturally can produce.

Clinic Testing and Experimental Results

The methods and devices disclosed herein are able to induce stem cell growth or functional restoration/healing. These evidences existed in multiple biofields.

a. Successful Cases (Table 1)

TABLE 1

| Organ | Specific Cases | Symptoms/Condition before Noxipoint Therapy | Outcome after Noxipoint |
|---|---|---|---|
| Plantar fasciitis (8 patients) | | Chronic and debilitating sharp heel pain exacerbated by bearing weight on the heel after prolonged periods of rest. Individuals with plantar fasciitis reported most intense pain occurred during their first steps after getting out of bed or after sitting for a prolonged period and subsequently improves with continued walking. Numbness, tingling, swelling, or radiating pains are rarely reported symptoms. | Fully functional in waling, running. Free of pain at any time. No pain reported weeks after the treatment (treatment session). |
| Heart valvular regurgitation (3 patients) | Case 1 & 2: Case 3: | Symptoms: Frequent shortness of breath, chest pressure. Mitral value regurgitation. Symptoms: Frequent shortness of breath, chest pressure. Evidences: Abnormal ECG and ultrasound results. | No more symptoms after 2 sessions of treatments Breath normally. After 2 sessions of treatments, Symptoms: None Evidences: Both ECG and ultrasound indicated normal. |
| Rheumatoid Arthritis (6 patients) | | Symptoms: Pain (often symmetric) at fingers and/or toes. Disfigured fingers/toes. | No more pain immediately and 3 months after 2-4 treatments |
| Acid Reflux (5 patients) | | Symptoms: Heartburn, Regurgitation | No more symptoms after 1-2 sessions of treatments |

TABLE 1-continued

| Organ | Specific Cases | Symptoms/Condition before Noxipoint Therapy | Outcome after Noxipoint |
|---|---|---|---|
| Interstitial Cystitis/bladder pain syndrome (IC/BPS) (1 case) | | Symptoms: Chronic severe and constant suprapubic pain, urinary frequency, painful sexual intercourse and nocturia. Evidence: fiberized/damaged urothelium (or bladder lining) | Normal urination and sexual intercourse after treatment. No more nocturia or pain after 2 treatments. Evidence: bladder normal. No more visible fiberization |
| Scoliosis (6 patients) | | Symptoms: curved spinal cord, ranging from 25 degree to 53 degree. Evidence: curved spine in X ray image | 4/6 patients had visibly straighter spine and all pain was removed after 2-7 treatments. Evidence: Two patients who had follow-up X rays indicating straighter spine. |
| Frozen shoulder/ Adhesive capsulitis of shoulder (100+ patients) | Refer to the IRB approved clinical trial report at Pain Cure Center | Movement of the shoulder (Range of motion) is severely restricted, with progressive loss of both active and passive range of motion. The condition is sometimes caused by injury, leading to lack of use due to pain, but also often arises spontaneously with no obvious preceding trigger factor. Painful in arm movements. | Ranges of motion became normal or nearly normal after 2-4 treatments. Pain-free movements. |
| Chronic cervical pain (200+ patients) | Refer to the IRB- approved clinical trial report at Pain Cure Center | Movement of the neck is moderately or severely restricted, with progressive loss of both active and passive range of motion. The condition is sometimes caused by injury, leading to lack of use due to pain, but also often arises spontaneously with no obvious preceding trigger factor. | Ranges of motion became normal or nearly normal after 2-4 treatments. Pain-free movements. |
| Migraine (15 patients) | 12 cases 3 cases | Periodic severe headache. Severe constant headache. | No more headache Symptom remained after 1-2 treatments. |
| Menstrual pain (5 patients) | | Periodic pain during menstrual periods | MP never recurred after 1-2 sessions in 4/5 cases. One patient who did not recover did not return after one treatment. |
| Cerebrovascular accident (CVA)/Strokes (5 patients) | | Unilateral paralysis of extremities. Stiffness of the affected area and pain during passive movement. | Passive pain and stiffness were relieved in all patients. Two patients regained movement/range of motion recovered after 4-6 sessions. | b. In Vitro Testing

In vitro testing shows that the substance P triggers the innate immune response, likely starting with the mast cell (MC) on site to release histamine and one type of cytokine, tumor necrosis factor-alpha (TNF-α). MC only releases TNF-α upon receiving the substance P signal, even though MC is also capable of producing other cytokines (e.g., Interlukin -1 (IL-1), IL-3, IL-4, IL-6). TNF-α recruits the macrophage to conduct phagocytosis on scar tissues or impaired cells and to release growth factors (such as insulin-like growth factor type 1, or IGF-1) that activate the differentiation of adult stem cells (e.g., satellite cells in the muscle) which in turn repair the impaired muscle/tissue. Other growth factors produced by the macrophage that are myogenic for satellite cells include transforming growth factor-beta (TGF-β) and basic fibroblast growth factor (FGF), which promote chemotaxis of satellite cells in the tissue toward the impaired site and inhibit them after activation.

An animal model test on rats in the lab proved that the present treatment process worked.

The Protocol:

The standard chronic pain model of acid injection is used as the baseline in the animal model test of the present treatment. Acid is injected into the left leg of six rats (unilateral injection) and induce chronic pain in both sides of hind paw. 6 rats are randomly divided into 3 groups (2 rats per group); 3 different stimulus intensities are applied on the left leg of 6 rats for 3 minutes: 1T, 2T and 3T Noxipoint stimulations. T is the stimulus threshold of muscle twitching. Note that this is translated from the earlier finding of human subject in terms of the relative intensity of Noxipoint stimulation between observed twitching (muscle contraction) and reported medium soreness.

Paw withdraw threshold of plantar hindpaw in the ipsilateral (A) and contralateral side (B) to the acid injection is used as the measurement of pain/functional deficit.

Before acid injection, rats could sustain with 15 g von frey stimulation applied on the plantar surface of hind paw. After acid injection, ipsilateral and contralateral side of hind paw skin became sensitized (withdraw threshold is down to 4-8 g).

Note that the acid injection (injecting acid twice at the leg muscle) has been used as the standard way to induce chronic pain. Once induced, the pain will stay for a long time. Most analgesic drugs could temporarily reduce the pain but could not maintain the result.

Figure 13:
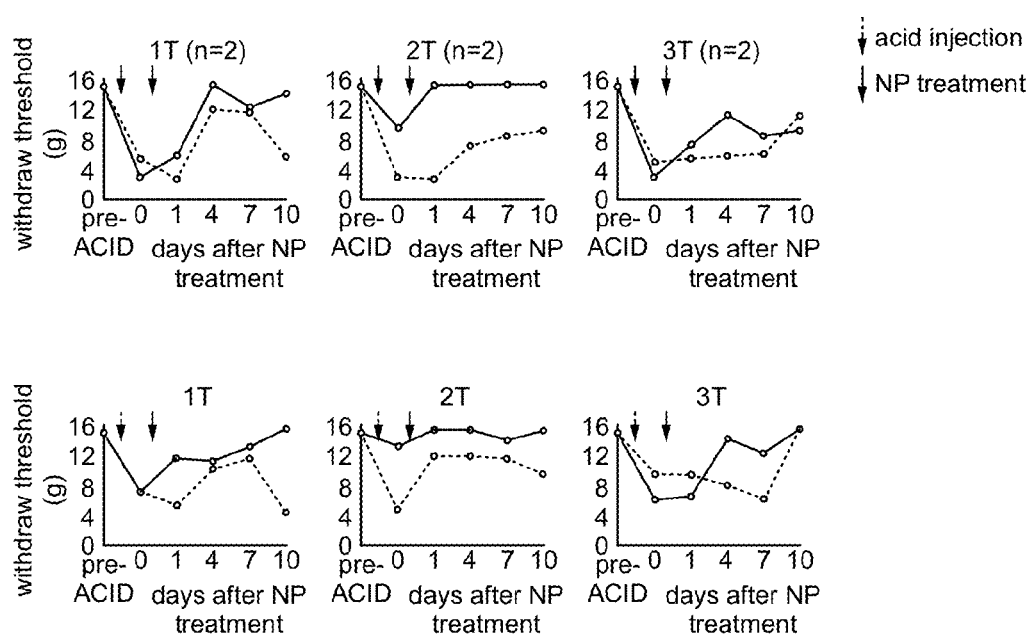
FIG. 13 illustrates a reversed paw sensitization and a restored function using a treatment in accordance with some embodiments.

Results:

As shown in FIG. 13, the present treatment is shown to have reversed the paw sensitization (withdraw threshold went back to 10-15 g) and restored the function persistently/permanently. Functional tests of treadmill test show similar results.

C. Clinical Evidences

It is shown that Noxipoint Process (NP) signaling pathway repairs and restores the muscle. A prospective, blinded randomized controlled clinical trial with crossover is conducted that compared the effect of NP versus conventional Physical Therapy including TENS (PT-TENS) on pain reduction, functional restoration and quality of life. To ensure that the functions are actually restored, the ranges of motion are measured by assessors after the each and last session of application of Noxipoint Process, 4-6 week after the last session. The pain level was also measured at the same time, and randomly followed up at 3-6 months after the treatment by phone.

At the follow-up (average 6 weeks after the last session), Noxipoint Process is found to restore all patients' functions to from an average impairment severity index of 10.3 (severe) to 2.3 (mild) ($p<0.001$) within three sessions of treatment. It is found to reduce the pain substantially (BPI from 7.7 to 0.8, $p<0.0001$) while patients in the PT-TENS arm showed no significant change (from 8.1 to 8.2, $p=0.84$). 75% of the Noxipoint Therapy patients are fully functional and free in all ranges of motion after 3 sessions of treatment. Quality of life measures showed significant comparative advantages of NT over PT-TENS ($p<0.0001$). The associated pain disappeared permanently as well.

Based on the clinical observations that (1) the pain was removed within minutes after each treatment, and (1) the full functions of the patient, measured by ranges of motion, were recovered a few days after NP treatment, the Noxipoint signaling pathway that caused cell remodeling (repair and/or regeneration) via adult stem cells was thus supported.

Multiple case studies on conditions otherwise intractable or untreatable by current medicine have shown the effectiveness of the novel Noxipoint process. Evidences showed that Noxipoint Process could restore functions of multiple organs besides the skeletomuscular ones, such as mitral valve prolapse (with ECG and ultrasound images before and after), kidney, bladder and stomach. When the underlying condition is resolved, the associated pain disappeared as well.

Such substantial outcomes in functional restoration are unprecedented. None of the existing treatments or remedies have generated results with such high curing rate and restoration rate.

Conclusion

Applying the Noxipoint device and/or drugs on the Noxipoint Signaling Pathway precisely at the Noxipoints of the impaired muscle triggers the adult stem cell growth and thus restores bodily functions on a permanent basis. As a derived benefit, it naturally eliminates the associated pain.

The drugs/chemicals including capcasin substance P, TNF-alpha, and/or growth factors such as IGF-1, applied on the dual Noxipoints that activate Noxipoint Signaling Pathway are novel and useful methods.

The electrical stimulation on the Noxipoint signaling pathway are novel for stem cell regeneration/functional recovery. The precise location (at Noxipoints) and unique sensory of the stimulation (soreness/dull pain) in Noxipoint Therapy make the difference.

In some embodiments, the terms Nocipoint and Noxipoint, and the prefixes noci- and noxi- are used interchangeably. In some embodiments, the term organ used herein comprises a collection of different tissues joined in structure unit to serve a common function. In some embodiments, the term organ used herein comprises a viscus, an internal organ, such as heart, liver, and intestine.

Noxipoint Therapy (NT) is useful and effective in reducing severe chronic pain, restoring bodily function, and improving quality of life with substantial and sustained effects in patients with severe chronic neck or shoulder pain. NT is significantly more effective than the conventional PT, including TENS. A signaling pathway from C-fiber through phagocytosis to satellite cell regeneration shows the clinical benefits.

In some embodiments, the stimulation on the Noxipoints/Nocipoints includes all forms of energy including IR (infrared), ultrasound, laser pulse, and any other forms of energy or stimulation.

In operation, the first and the second Noxipoints are identified and an amount of stimulations are applied on the Noxipoints with a predetermined chemical dosage or a predetermined electrical voltage with a preselected intensity, wave length, frequency, wave pattern or a combination thereof.

The present invention has been described in terms of specific embodiments incorporating details to facilitate the understanding of principles of construction and operation of the invention. Such reference herein to specific embodiments and details thereof is not intended to limit the scope of the claims appended hereto. It is readily apparent to one skilled in the art that other various modifications can be made in the embodiment chosen for illustration without departing from the spirit and scope of the invention as defined by the claims.

NT Versus Shame Therapy On Mechanical Hyperalgesia Of The Rat

Figure 12F:
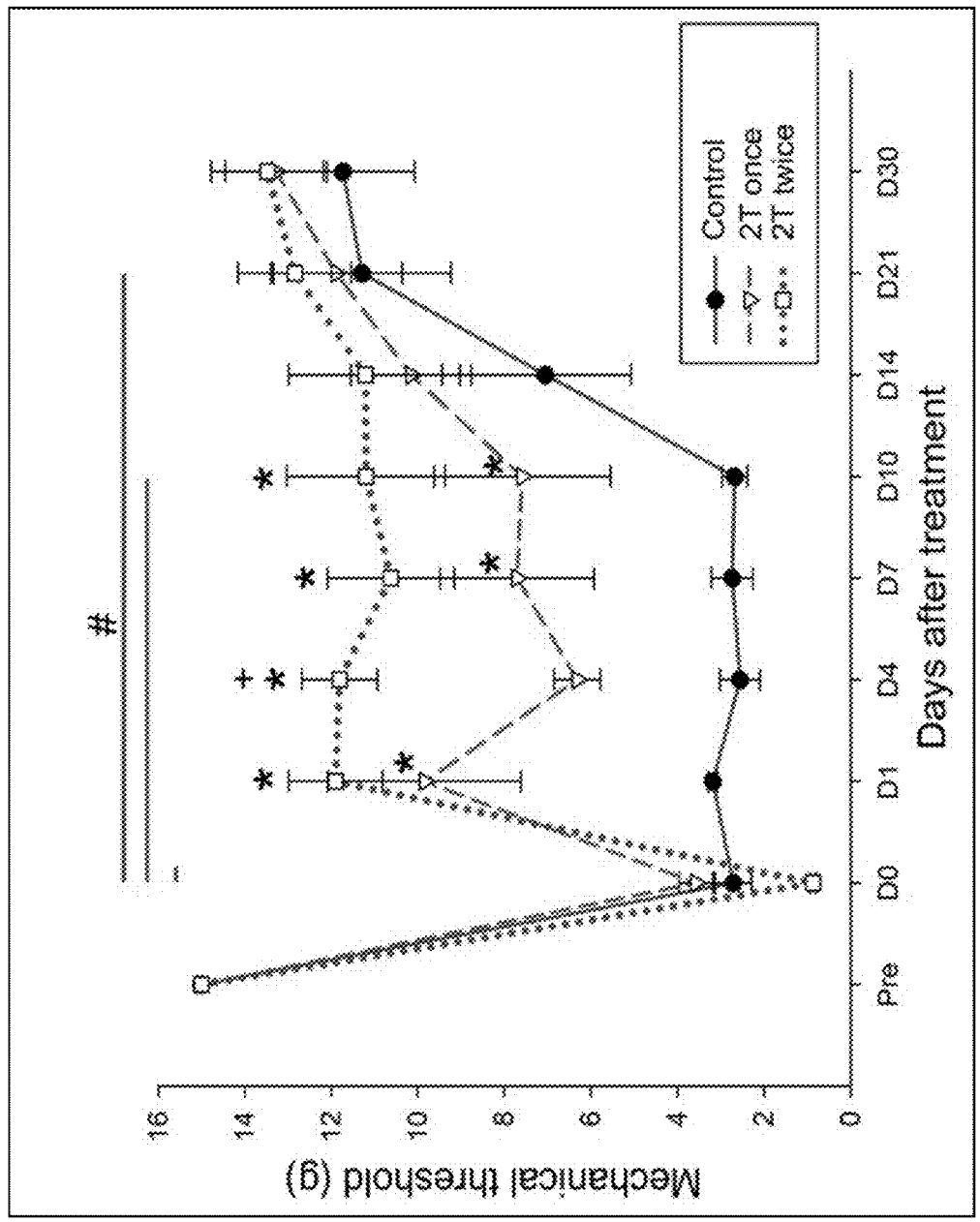
FIG. 12F illustrates the result of NK-like treatment to chronic hypersensitivity in a rat study in accordance with some embodiments.

FIG. 12F illustrates the result of NK-like treatment to chronic hypersensitivity in a rat study in accordance with some embodiments of the present invention.

Methods

Randomized controlled experiment of NT-like procedure versus sham control is performed on adult male Sprague-Dawley rats, which are purchased from BioLasco Company in Taiwan. Groups of 2 to 3 rats are housed together in plastic cages and are placed in a temperature- and humidity-controlled room ($23\pm2°$ C. and $55\pm5\%$) with a 12-h light/dark cycle (lights on at 06:00 h). Food and water are available ad libitum. All animal care and experimental procedures are approved by the Institutional Animal Care and Use Committee of National Taiwan University (Approval No. NTU-103-EL-69). The study adhered to guidelines established by the Codes for Experimental Use of Animals from the Council of Agriculture of Taiwan, based on the Animal Protection Law of Taiwan.

The rats weighed between 260 and 400 g at the beginning of the experiment. The repeated acid-injection-produced hyperalgesia model is used to induce chronic mechanical hyperalgesia following the Sluka model. Acidic saline (pH 4.0) is prepared by adding HCl droplets to sterile saline. Two dosages of 100 μL of this acidic saline solution are injected into the mid-belly of the left gastrocnemius muscle of the rat under 4% isoflurane anesthesia. The two i.m. injections are separated by an interval of 5 days. Mechanical sensitivity is assayed by the threshold force eliciting a lift of the hind limb by von Frey filament (North Coast Medical, Inc., Morgan Hill, USA) stimulation of the heel region of the left hind paw. Each rat is individually placed on an elevated wire mesh floor in the transparent acrylic box (dimensions 21 cm×12 cm×14 cm) and allowed to acclimate and withstood 15 g filament stimulation before starting acid injections. On each test day, the rat is placed in the same chamber to acclimate 10 min. We applied the von Frey filaments of various bending forces (0.6, 1, 2, 4, 6, 8, and 15 g). Brisk withdrawal or paw flinching is regarded as positive response. Threshold force is determined with the up-down procedure by Chaplan et al.

NT-like treatment starts on the third day after the second acid injection. The same stimulator and the same stimulation parameters in the patient treatment are used. The two poles of the stimulation are connected to two separated pieces of aluminum foil of different widths. Under 4% isoflurane anesthesia, the wider foil is wrapped around the origin of the gastrocnemius muscle, and the narrower one around the neck region of the ankle (e.g., the insertion of the gastrocnemius muscle). Both pieces are half-circle shaped and care is taken to secure the contact of the half circle to the gastrocnemius part of the leg. The electrical stimulation is applied for three minutes. The threshold intensity that elicited ipsilateral lower leg contraction is defined as 1T, and intensity (measured through an oscilloscope) of 2T is applied as NT-like treatment, based on the relative intensities of NT stimulation observed in human patients, where to effective setting for NT is about 1.5T to 2T (FIG. 12E). One of the two test groups is treated with NT once on Day 0, and the other group treated by NT twice on Day 0 and Day 3 respectively. The sham group underwent the same procedure of anesthesia and electrode placement yet without stimulation. Mechanical threshold of the hind paws to von Frey stimulation is measured on 1, 4, 7, 10, 14, and 21 days after the NT-like treatment. The window of observation of the induced hyperalgesia (Days 0-10) is dictated by the time when the control group naturally exhibited reduced sensitivity (after Day 10). Two-Way Repeated Measures ANOVA (One Factor Repetition) followed by pairwise multiple comparison procedures (Tukey Test) is used to analyze the data.

Results

NT-like therapy significantly reverses mechanical sensitization of the hind paw of rats (80.7% reduction in 2T-twice group at Day 3 and persisted through Day 30; $p<0.01$) (See FIG. 12F), while the sham therapy does not cause any change in the mechanical sensitization. It confirmed the findings in human clinical trials.

In FIG. 12F, NT-like therapy reverses mechanical sensitization of the hind paw, which is produced by repeated injection of acid (pH=4) solution into the gastrocnemius muscle of the rat. On the third day after the second acid injection and a stable development of mechanical sensitization (indicated by the drop of threshold force that produced hind paw withdrawal from 15 g to less than 4 g on Day 0), NT-like treatment is given to the afflicted muscle at twice the threshold intensity that caused gastrocnemius contraction (2T). Three groups of rats (2T twice, 2T once, and sham control; 6 rats each) are tested. The treatment day is denoted as Day 0. Note that NP treatment for two times (2T twice, the red line) reversed mechanical sensitization of D1, D4, D7 and D10. In the FIG. 12F, data using "*" refers to significantly different NT outcome ($p<0.01$) in comparison with sham value on the matching days. Data using "+" refers to significantly different NT outcome ($p<0.01$) in comparison with 2T-once group. Data using "#" refers to significantly different NT outcome ($p<0.01$) in comparison with threshold value before the acid injection (pre). Two-Way Repeated Measures ANOVA (One Factor Repetition) followed by pairwise multiple comparison procedures (Tukey Test) are used.

In some embodiments, the testing results show that the optimal intensity for most of both human and rats is between 1T and 2T, though >2T worked in some cases. In some embodiments, the presence of vibration/contraction of a muscle (at intensity T) is used as a predicate to control the optimal setting of the NT stimulation (e.g., slow down the increment of the intensity at T, and slow down further after it reaches 1.5T or completely stop at 2T).

Figure 14:
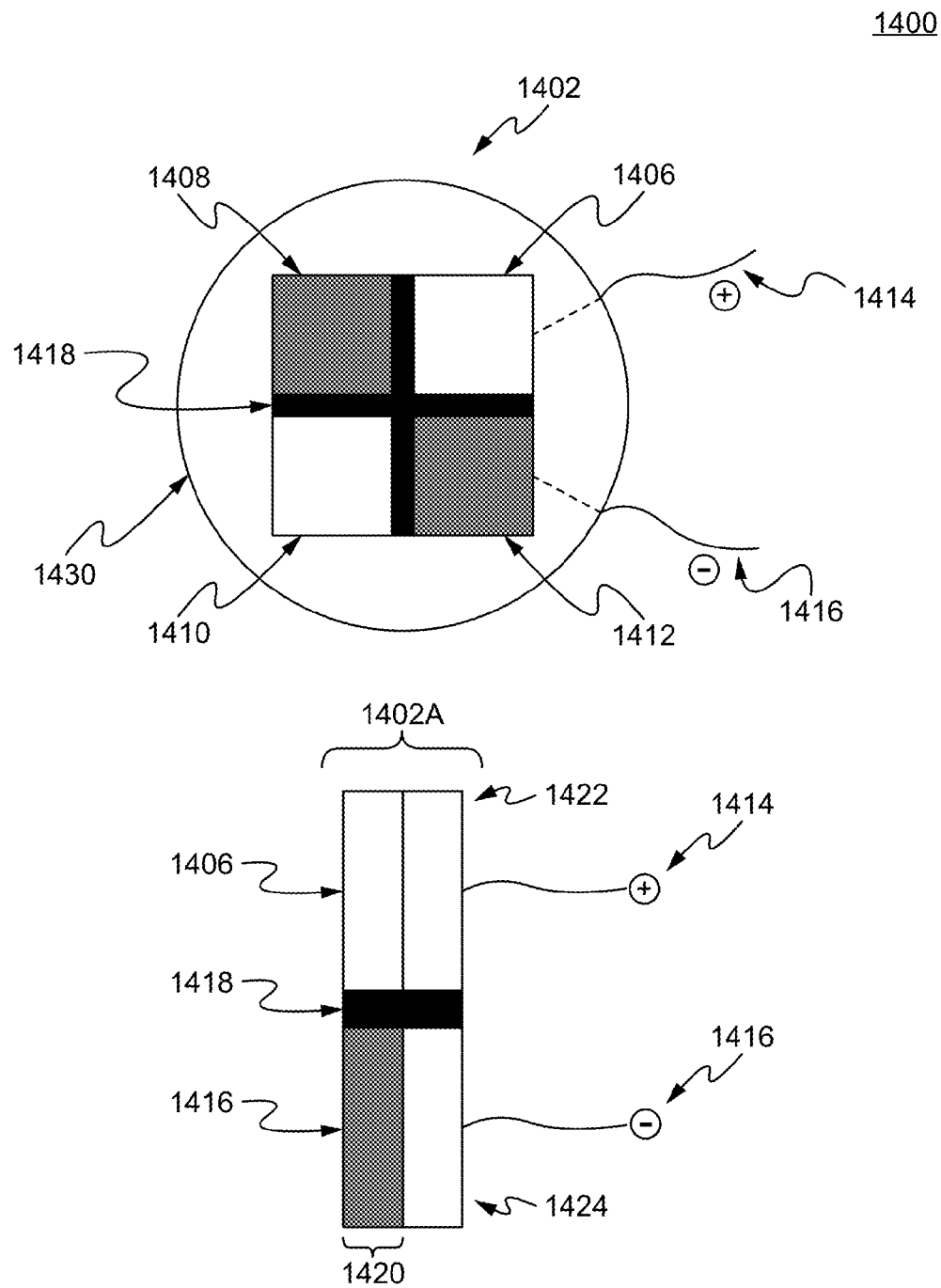
FIG. 14 illustrates a Noxipoint stimulating matrix pad in accordance with some embodiments.

FIG. 14 illustrates a Noxipoint stimulating matrix pad 1400 in accordance with some embodiments. In some embodiments, the Noxipoint stimulating matrix pad 1400 comprises an electrode pad 1402. In some embodiments, the electrode pad 1402 comprises a grid of electrodes. For example, a 2×2 grid of electrodes 1406, 1408, 1410, and 1412. The electrodes are electrically isolated/separated by an insulating material, such as a separating member 1418. In some embodiments, the insulating material comprises polymers, plastics, insulation gels, and/or resin, such as polyethylene, polypropylene, and acrylnitrile butadiene styrene. In some embodiments, the grid of electrodes are constructed in various forms, patterns, and numbers, such as a matrix of 1×1, 2×1, 3×3, . . . 10,000×100,000. Each side of the top surface area of the electrodes can range from 0.1 micrometer to 30 cm, such as 10 mm, 1 cm, 10 cm.

In some embodiments, a single pair of electrodes are used for the Noxipoint stimulation. In other embodiments, multiple pairs of the electrodes are used for the Noxipoint stimulation. Each pair of the electrodes are able to be applied a voltage of different phases. For example, a positive phase and negative phase of voltages are supplied through the electrical wires 1414 and 1416. The electrical wires 1414 and 1416 are able to be directly coupled with the electrodes 1406 and 1412. In some embodiments, the electrical wires 1414 and 1416 are coupled with the electrode pad 1402 through a voltage/current distributor, which distribute the voltage/electrical current to each or preselected electrodes. For example, the voltage is selected to be applied to electrodes 1408 and 1406 only. In another example, the voltage is selected to be applied to electrodes 1406, 1408, 1410, and 1412, which can be applied concurrently or alternatively in sequence. In some embodiments, different voltages are applied to different electrodes. In other embodiments, same voltages are applied to different electrodes. In some embodiments, the electrodes 1406, 1408, 1410, and 1412 are on a hosting member, such as a fabric sheet 1430. A person of ordinary skill in the art appreciates that any voltages applying patterns, magnitudes, durations, or a combination thereof are within the scope of the present disclosure.

The structure of 1402A is a side view of the electrode pad 1402. As shown, the wires 1414 and 1416 are coupled with voltage distributors 1422 and 1424. A person of ordinary skill in the art appreciates that the voltage distributors 1422 and 1424 are able to be constructed to any structures, any patterns, and with any conducting materials. For example, the voltage distributors 1422 and 1424 are structured to control and/or distribute currents from the wires 1414 and 1416 to a pair of preselected electrodes, a region of preselected electrodes, or all electrodes. The software and hardware disclosed above, such as for finding or guiding the finding of a pair of Noxipoints, are used to determine which electrodes (e.g., number and location of electrodes are engaged for applying voltage) are selected as voltage applying points.

Figure 15:
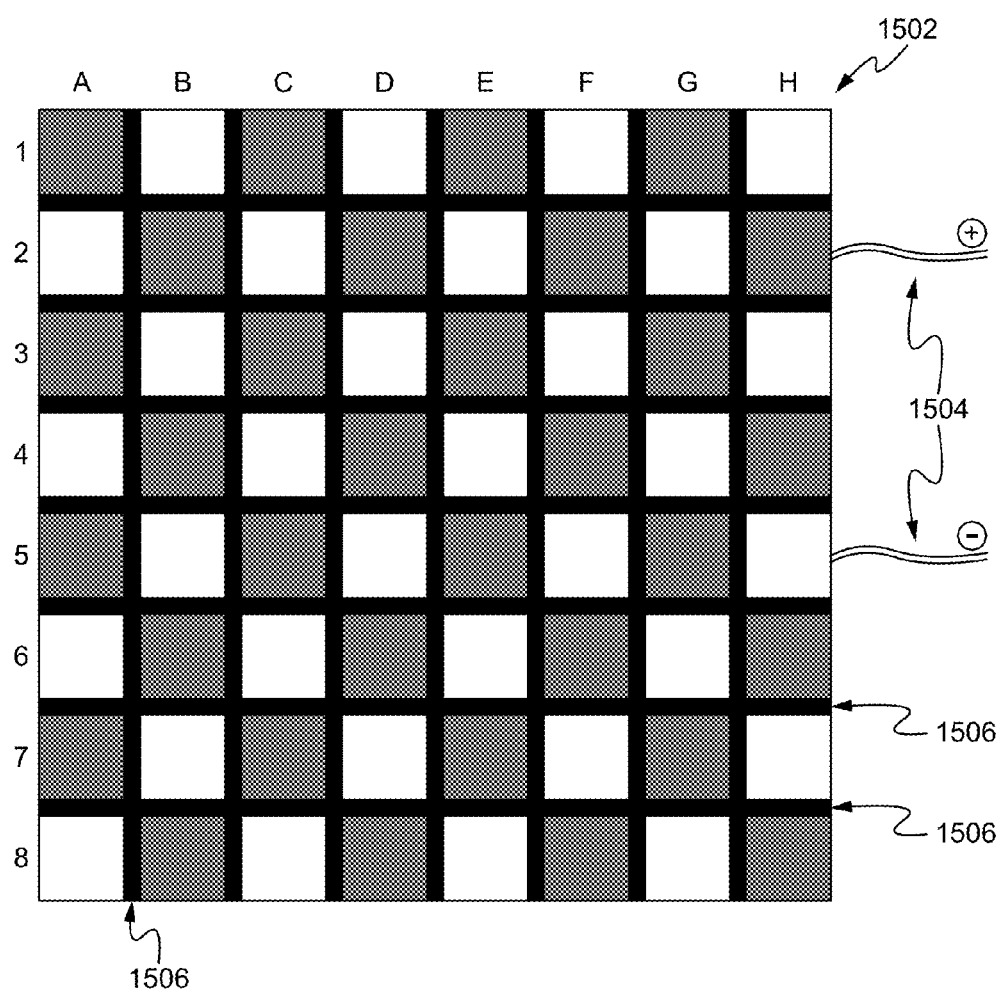
FIG. 15 illustrates a Noxipoint stimulating pad in accordance with some embodiments.

FIG. 15 illustrates a Noxipoint stimulating pad 1500 in accordance with some embodiments. In some embodiments, the Noxipoint stimulating pad 1500 comprises an electrode sheet 1502. For the purpose of illustration, the columns are numbered from A to H and the rows are numbered from 1 to 8. Each of the square areas represents an electrode. In some embodiments, each of the square areas represents a cluster of electrodes (e.g., 200 electrodes of the same phase). An insulation material 1506 separates each of the electrodes preventing the electrode from forming a short. An electrical voltage is supplied by the wires 1504. One or more voltages are able to be selected to be applied on any of the selected electrodes.

In an example, the Noxipoint stimulating pad 1500 is being applied on a forearm muscle. The device disclosed herein determines that a pair of Noxipoints located at the location corresponding to the electrodes of B2 and F7. The device is able to apply a pulsed voltage of +100V and −100V to B2 and F7 respectively for a predetermined duration, such as 20 minutes. In some embodiments, the device is configured by computer software to identify at least a pair of Noxipoints for applying one or more voltages to stimulate the Noxipoints.

In some embodiments, the device disclosed herein applies multiple same or different voltages to multiple pairs of electrodes, such as +100V at C2, −100V at E3, +60V at F1, and −60V at H6. The voltages applied to multiple pairs of electrodes can be applied concurrently, in sequence, randomly, or in any other patterns.

Figure 16:
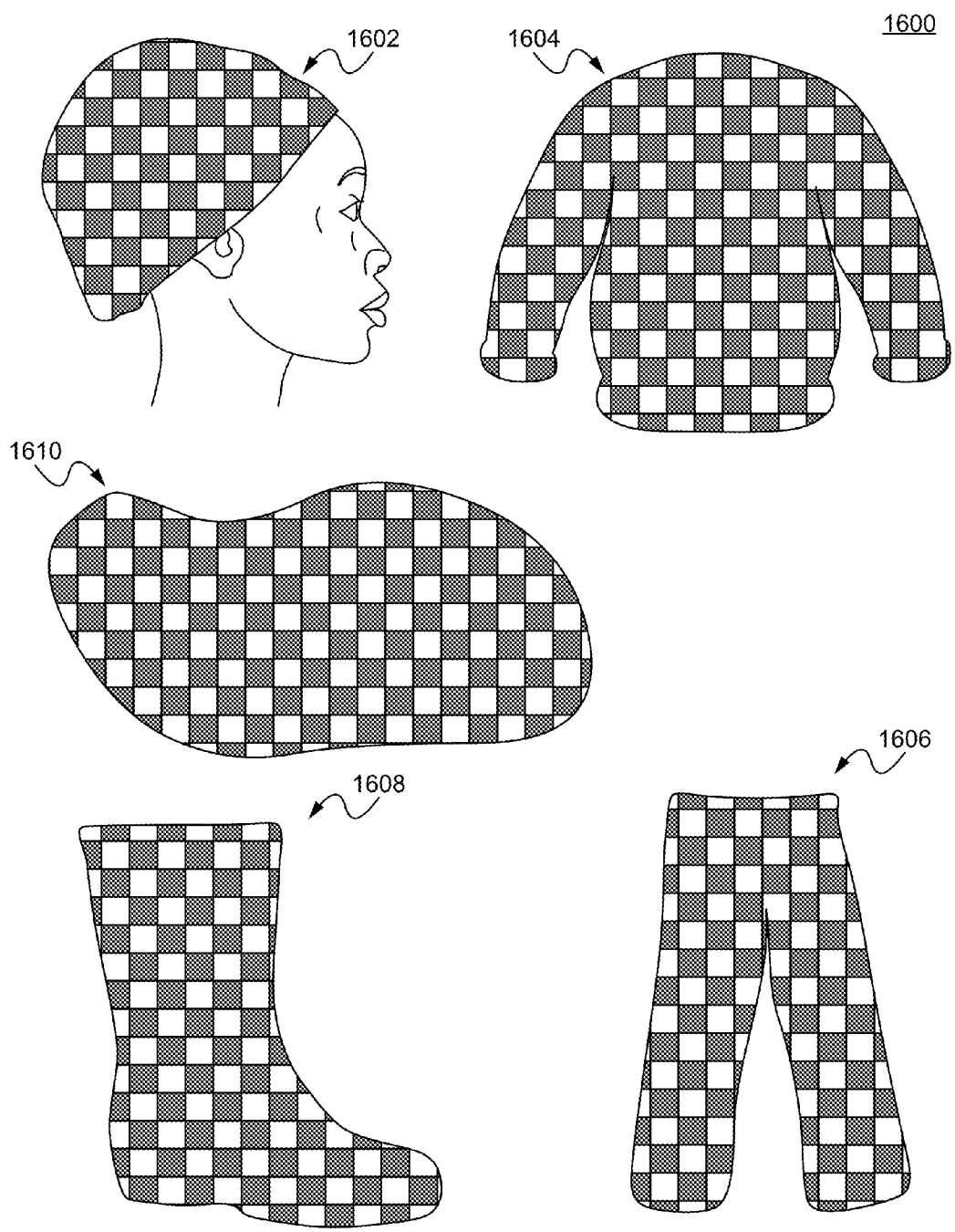
FIG. 16 illustrates Noxipoint stimulating devices in accordance with some embodiments.

FIG. 16 illustrates Noxipoint stimulating devices 1600 in accordance with some embodiments. The devices 1600 are constructed into various wearable structures, such as a hat 1602, a cloth 1604, a pair of pants 1606, a pair of boots 1608, and a flexible/elastic sheet 1610. The voltage can be applied at any predetermined pair of electrodes.

In utilization, the device is used to stimulate one or multiple pairs of Noxipoints.

In operation, the electrodes are placed on a portion of a person's body and a predetermined voltage is applied to at least a pair of electrodes on Noxipoints for a predetermined duration, such as 3 or 30 minutes.

The present invention has been described in terms of specific embodiments incorporating details to facilitate the understanding of principles of construction and operation of the invention. Such reference herein to specific embodiments and details thereof is not intended to limit the scope of the claims appended hereto. It is readily apparent to one skilled in the art that other various modifications can be made in the embodiment chosen for illustration without departing from the spirit and scope of the invention as defined by the claims. Features in various examples or embodiments are applicable throughout the Present Specification.

What is claimed is:

1. A method of Noxipoint stimulation comprising:
   a) forming multiple electrodes on a hosting member; and
   b) coupling an electrical power source to the multiple electrodes.

2. The method of claim 1, further comprising:
   a) identifying a pair of Noxipoints, wherein the pair of Noxipoints are located at two terminal ends of a muscle fiber; and
   b) applying a predetermined electrical or chemical stimulation to the pair of Noxipoints.

3. The method of claim 1, further comprising using an electrical control circuit configured to adjust a pulse pattern applied to the Noxipoints.

4. The method of claim 3, wherein the electrical control circuit is configured to adjust a pulse duration applied to the Noxipoints.

5. The method of claim 3, wherein the electrical control circuit is configured to adjust a pulse strength applied to the Noxipoints.

6. The method of claim 3, wherein the electrical control circuit is configured to generate an anatomic site specific stimulation.

7. The method of claim 3, wherein the electrical control circuit is configured to generate an intensity and submodality-specific stimulation.

8. The method of claim 7, wherein the submodality comprises a moderate soreness, an achiness, a deep-muscle tenderness or a mild dull pain.

9. The method of claim 1, wherein the Noxipoints are on an organ.

10. The method of claim 3, wherein the electrical control circuit is configured to trigger a reaction of a neuroimmune cascade at the pair of Noxipoints.

11. The method of claim 1, further comprising a user interface configured to adjust an electrical stimulation at the pair of Noxipoints.

12. The method of claim 1, wherein the multiple electrodes are structured to form a matrix of electrodes.

13. The method of claim 1, wherein the multiple electrodes are configured to apply alternative phases of applied voltages.

14. The method of claim 1, wherein the hosting member is a wearable electronic device.

15. The method of claim 1, further comprising applying an electrical voltage to at least two preselected electrodes among the multiple electrodes, wherein the at least two preselected electrodes are determined to be at or near locations of Noxipoints.

16. An electrical treatment device comprising:
   a) a hosting member having multiple electrodes;
   b) a user-controllable device containing a user control panel; and
   c) an electrical control circuit coupled with the hosting member configured to adjust an applied electrical stimulation based on an input received at the user controlling device.

17. The device of claim 15, wherein the electrical control circuit is configured to apply a predetermined electrical power to the pair of Noxipoints.

18. The device of claim 15, wherein the hosting member comprises a wearable electronic device.

19. The device of claim 15, wherein the wearable electronic device comprises a hat.

20. The device of claim 15, wherein the wearable electronic device comprises pants, a boot, a cloth, or a combination thereof.

21. The device of claim 12, wherein the multiple electrodes are structured in a grid.

22. A method of using a Noxipoint stimulation device comprising:
   a) preparing a wearable electronic device containing multiple electrodes;
   b) coupling an electrical power source to the multiple electrodes;
   c) identifying a pair of Noxipoints; and
   d) applying a predetermined electrical or chemical stimulation to the pair of Noxipoints.

23. The method of claim 21, wherein the pair of Noxipoints are located at two terminal ends of a muscle fiber.

24. The method of claim 21, wherein the pair of Noxipoints are located at two terminal ends of an organ.

25. The method of claim 21, further comprising a computer software configuring the device for the identifying the pair of Noxipoints.

* * * * *